United States Patent
Yamato et al.

(10) Patent No.: US 7,632,957 B2
(45) Date of Patent: Dec. 15, 2009

(54) ESTERIFICATION REACTION PRODUCTS AND COSMETIC PRODUCTS

(75) Inventors: Yoshihito Yamato, Yokohama (JP); Yukiko Oi, Yokohama (JP); Masaaki Fujisawa, Yokohama (JP)

(73) Assignee: The Nisshin OilliO Group, Ltd., Tokyo (JP)

(*) Notice: Subject to any disclaimer, the term of this patent is extended or adjusted under 35 U.S.C. 154(b) by 118 days.

(21) Appl. No.: 11/883,116

(22) PCT Filed: Jan. 26, 2006

(86) PCT No.: PCT/JP2006/301212

§ 371 (c)(1), (2), (4) Date: Jul. 26, 2007

(87) PCT Pub. No.: WO2006/080389

PCT Pub. Date: Aug. 3, 2006

(65) Prior Publication Data

US 2008/0260663 A1 Oct. 23, 2008

(30) Foreign Application Priority Data

Jan. 28, 2005 (JP) ............................. 2005-021095
Jun. 10, 2005 (JP) ............................. 2005-170370
Sep. 2, 2005 (JP) ............................. 2005-255030
Oct. 13, 2005 (JP) ................. PCT/JP2005/018856

(51) Int. Cl.
*C07C 59/00* (2006.01)

(52) U.S. Cl. ........................... 554/213; 424/59; 424/61; 424/70.1

(58) Field of Classification Search ................. 554/213; 424/59, 61, 70.1
See application file for complete search history.

(56) References Cited

U.S. PATENT DOCUMENTS

| | | | |
|---|---|---|---|
| 3,890,358 A | 6/1975 | Hutchison et al. | |
| 5,840,943 A | 11/1998 | Ansmann et al. | |
| 2004/0191282 A1 | 9/2004 | Fujino et al. | |
| 2005/0118210 A1 | 6/2005 | Kachi et al. | |

FOREIGN PATENT DOCUMENTS

| | | |
|---|---|---|
| DE | 44 20 516 A1 | 12/1995 |
| JP | 49-020341 A | 2/1974 |
| JP | 52-48613 * | 4/1977 |
| JP | 52-048613 A | 4/1977 |
| JP | 53-127841 A | 8/1978 |
| JP | 54-109917 A | 8/1978 |
| JP | 54-049337 A | 4/1979 |
| JP | 54-109917 * | 8/1979 |
| JP | 55-057509 A | 4/1980 |
| JP | 56-108739 A | 8/1981 |
| JP | 56-115740 * | 9/1981 |
| JP | 56-115740 A | 9/1981 |
| JP | 61-056113 A | 3/1986 |
| JP | 64-090025 A | 4/1989 |
| JP | 05-331023 A | 12/1993 |
| JP | 07-008781 A | 1/1995 |
| JP | 07-223925 A | 8/1995 |
| JP | 10-067889 A | 3/1998 |
| JP | 10-120833 A | 5/1998 |
| JP | 10-273433 A | 10/1998 |
| JP | 2000-095666 A | 4/2000 |
| JP | 2000-290232 * | 10/2000 |
| JP | 2000-290232 A | 10/2000 |
| JP | 2003-104843 A | 4/2003 |
| JP | 2003-212747 A | 7/2003 |
| JP | 2004-331573 A | 11/2004 |
| WO | WO 03/015741 A1 | 2/2003 |

OTHER PUBLICATIONS

U.S. Appl. No. 11/883,089, filed Jul. 26, 2007, Confirmation No. 9471.
Y. Yamato et al, "The characteristic of a new water holding material, and application to cosmetics", *Fragrance Journal*, vol. 33, pp. 53-59 (2005) (Chemical Abstracts, abstract only).
Keshoshin-Jiten (Cosmetic Dictionary), Maruzen, p. 8 (2003).
English language International Preliminary Report on Patentability PCT/IB/373 (one page) and PCT/ISA/237 (3 pages) issued Jul. 31, 2007 in International Application PCT/JP2006/301212.

* cited by examiner

*Primary Examiner*—Deborah D Carr
(74) *Attorney, Agent, or Firm*—Frishauf, Holtz, Goodman & Chick, P.C.

(57) ABSTRACT

An esterification reaction product obtained by esterifying dipentaerythritol and a 12-hydroxystearic acid polymer and having a hydroxyl value of 20 to 70 mg KOH/g and an acid value of 3 mg KOH/g or less. The esterification reaction product has a high-water holding property and a pigment-dispersing property.

11 Claims, 7 Drawing Sheets

ESTERIFICATION REACTION PRODUCTS AND COSMETIC PRODUCTS

This application is the United States national phase application of International Application PCT/JP2006/301212 filed Jan. 26, 2006.

TECHNICAL FIELD

The present invention relates to esterification reaction products. Specifically, the present invention relates to esterification reaction products having good adhesion to skin and being excellent in waterproof-film-forming ability, pigment-dispersing properties, water-holding properties, non-dyeing properties, and long-term stability.

The present invention also relates to cosmetic products containing the esterification reaction products.

BACKGROUND ART

Cosmetic products have been conventionally used for imparting good appearance to skin or the like. In addition, cosmetic products are used for protecting skin from drying by preventing transpiration of moisture from the skin and further conditioning the skin as well as giving good appearance to skin or the like.

Natural oils such as lanolin and castor oil and synthetic ester oils having water-holding ability have been widely used as raw materials for obtaining cosmetic products which can prevent skin from drying and condition skin. In particular, water-in-oil-type cosmetic products coat a skin surface with an oil film and have higher affinity to skin compared to oil-in-water-type cosmetic products, and are therefore widely used as cosmetic products that can prevent skin from drying and condition skin.

Conventionally, lanolin has been widely used as an oil of natural origin. Lanolin is derived from wool fat and has high affinity, adhesion, and humectant properties to skin. Furthermore, lanolin is excellent in water-holding and emulsifying properties. Therefore, lanolin has been widely used in basic cosmetics, makeup cosmetics, and many other cosmetic products (refer to, for example, Non-Patent Document 1).

However, the use of raw materials derived from animals is decreasing because of the recently occurred mad cow disease problems, and it is significantly decreased to directly use animal-derived raw materials in cosmetic products. In addition, natural products such as lanolin and castor oil have problems that a constant quality cannot be readily obtained and prices widely fluctuate. Thus, they are not stable raw materials in the quality and price.

Consequently, instead of natural oils, synthetic ester oils have been recently used. For example, ester compounds of 12-hydroxystearic acid and polyols (refer to, for example, Patent Documents 1 to 4) and ester compounds of 12-hydroxystearic acid polymers and polyols (refer to, for example, Patent Documents 5 to 9) have been developed. The synthetic ester oils disclosed in these Patent Documents can impart water-holding properties to products containing these oils.

However, water-in-oil-type cosmetic products prepared using the ester compounds disclosed in Patent Documents 1 to 7 have unstable water-holding states, and thereby the long-term stability and the pigment-dispersing properties of the cosmetic products may be deteriorated. Furthermore, though cosmetic products prepared using the ester compounds disclosed in Patent Documents 1 to 7 can well adhere to skin and also have waterproof-film-forming abilities and non-dyeing properties at certain degrees, it is desired to further improve these properties.

In addition, the ester compounds disclosed in Patent Documents 8 and 9 are emulsifying agents and do not have film-forming ability, which oils do. Furthermore, the amounts of these esters used in cosmetic products may be restricted depending on types of the cosmetic products.

Patent Document 1: Japanese Unexamined Patent Publication No. 52-48613
Patent Document 2: Japanese Unexamined Patent Publication No. 54-109917
Patent Document 3: Japanese Unexamined Patent Publication No. 55-57509
Patent Document 4: Japanese Unexamined Patent Publication No. 56-57509
Patent Document 5: Japanese Unexamined Patent Publication No. 56-108739
Patent Document 7: Japanese Unexamined Patent Publication No. 05-331023
Patent Document 9: Japanese Unexamined Patent Publication No. 2000-290232
Patent Document 6: Japanese Unexamined Patent Publication No. 64-90025
Patent Document 8: Japanese Unexamined Patent Publication No. 07-8781

Non-Patent Document 1: Keshohin-Jiten (Cosmetic Dictionary), Maruzen, published on Dec. 15, 2003 (Heisei 15)

DISCLOSURE OF INVENTION

Problems to be Solved by the Invention

An object of the present invention is therefore to provide an esterification reaction product having good adhesion to, for example, skin and being excellent in waterproof-film-forming ability, pigment-dispersing properties, water-holding properties, non-dyeing properties, and long-term stability.

Further, an object of the present invention is to provide an esterification reaction product which can be used for manufacturing cosmetic products (oil-in-water-type emulsion cosmetic products and water-in-oil-type emulsion cosmetic products) which can contain a large amount of water (and polyols) and are good in water-retaining stability and long-term stability.

Further, an object of the present invention is to provide a cosmetic product having good adhesion to skin or the like and being excellent in waterproof-film-forming ability, pigment-dispersing properties, softness, moisturizing properties, water-holding properties, non-dyeing properties, and long-term stability.

Further, an object of the present invention is to provide a cosmetic product excellent in adhesion to, for example, skin or hair, emollient effects, and long-lasting makeup effects.

Means for Solving the Problem

The present inventors have conducted intensive studies to achieve the above-mentioned objects and have found the fact that the above-mentioned objects can be achieved by using a specific esterification reaction product. Thus, the present invention has been accomplished.

The present invention provides an esterification reaction product obtained by esterifying dipentaerythritol and a 12-hydroxystearic acid polymer. The esterification reaction product has a hydroxyl value of 20 to 70 mg KOH/g and an acid value of 3 mg KOH/g or less.

The present invention also provides a cosmetic product containing such an esterification reaction product.

ADVANTAGEOUS EFFECT OF THE INVENTION

According to the present invention, an esterification reaction product excellent in properties for holding water and dispensing, for example, a pigment is provided.

By using the above-mentioned esterification reaction product, oil-in-water-type and water-in-oil-type emulsion cosmetic products containing a large amount of water (and/or a polyol) and having high water-retaining and long-term stabilities can be provided. In the present invention, the high water-holding properties of the esterification reaction product can be confirmed that a water-holding material composed of the esterification reaction product and water at a mass ratio of 7:3 shows no endothermic peak due to water at about 0° C. in differential scanning calorimetry. Furthermore, the cosmetic product according to the present invention can hold not only a large amount of water but also water-soluble polyols such as glycerin, which do not have compatibility to water. In the present invention, the term "polyol" means glycerin and polymers thereof; glycols such as polyethylene glycol, propylene glycol, and 1,3-butylene glycol; and saccharides such as xylitol, sorbitol, and maltitol. In addition, products containing the esterification reaction product according to the present invention can hold not only water but also aqueous solutions dissolving, for example, inorganic salts, organic salts, water-soluble agents, or animal or plant extracts therein. Specifically, examples of the inorganic salts include sodium chloride, potassium chloride, calcium chloride, magnesium chloride, sodium sulfate, magnesium sulfate, sodium carbonate, sodium hydrogen carbonate, and sodium phosphate. Examples of the organic salts include sodium citrate, sodium malate, sodium gluconate, sodium lactate, sodium succinate, and sodium tartrate. Examples of the water-soluble agents include skin-lightening agents. Examples of the skin-lightening agents include ascorbic acid and/or derivatives thereof, such as L-ascorbic acid glucoside, L-ascorbic acid-2-phosphate ester, L-ascorbic acid-3-phosphate ester, L-ascorbic acid-6-phosphate ester, L-ascorbic acid-2-polyphosphate ester, L-ascorbic acid-2-sulfate ester, L-ascorbic acid-2-palmitate ester, L-ascorbic acid-6-palmitate ester, L-ascorbic acid-2-stearate ester, L-ascorbic acid-6-stearate ester, L-ascorbic acid-2,6-dibutyl ester, L-ascorbic acid-2,6-dipalmitate ester, and salts thereof. Examples of the salts include sodium salts, potassium salts, magnesium salts, calcium salts, barium salts, ammonium salts, monoethanolamine salts, diethanolamine salts, triethanolamine salts, monoisopropanolamine salts, and triisopropanolamine salts. Other examples of the skin-lightening agent include arbutin, kojic acid, and glutathione. Examples of water-soluble agent include anti-inflammatory agents. Examples of the anti-inflammatory agents include glycyrrhizinic acid derivatives and allantoin. Examples of the animal or plant extracts include Nettle leaf extract, Siberian ginseng extract, Phellodendron bark extract, Coffea Arabica extract, White birch extract, Mentha piperita extract, Thymus extract, Tea extract, Hamamelis extract, Isodonis japonica extract, Coltsfoot extract, Vitis vinifera leaf extract, Humulus lupulus extract, Horse chestnut extract, Melissa officinalis extract, Acerola extract, Rose fruit extract, Actinidia chinensis fruit extract, Arnica extract, Scutellaria baicalensis root extract, Coptis rhizome extract, Lamium album extract, Cattail extract, Chamomilla recutita extract, Artemisia capillaris flower extract, Glycyrrhiza glabra extract, Gardenia florida extract, Sasa veitchii extract, Gentiana extract, Clammellia sinensis extract, Symphytum officinale leaf extract, Perilla ocymoides leaf extract, Lithospermum erythrorhizone root extract, Linden extract, Spiraea ulmaria extract, Paeonia albiflora root extract, Lonicera japonica extract, Salvia officinalis extract, Hedera helix extract, Sambucus nigra flower extract, Achillea millefolium extract, Swertia japonica extract, Mulberry root extract, Calendula officinalis flower extract, Eriobotrya japonica leaf extract, Prunus persica leaf extract, Centaurea cyanus flower extract, Saxifrage sarmentosa extract, Mogwort extract, Lactuca scariola sativa extract, Anthemis nobilis flower extract, and Sanguisorba officinalis root extract. In the present invention, the above-mentioned inorganic salts, organic salts, water-soluble agents, and animal or plant extracts may be used alone or in a combination of two or more thereof.

By using the esterification reaction product according to the present invention, a cosmetic product having good adhesion to, for example, skin and excellent waterproof-film-forming ability, pigment-dispersing properties, softness, moisturizing properties, water-holding properties, non-dyeing properties, and long-term stability can be provided.

In addition, by using the esterification reaction product according to the present invention, a cosmetic product excellent in adhesion to, for example, skin or hair, emollient effects, and long-lasting makeup effects can be provided.

BEST MODE FOR CARRYING OUT THE INVENTION

Figure 1:
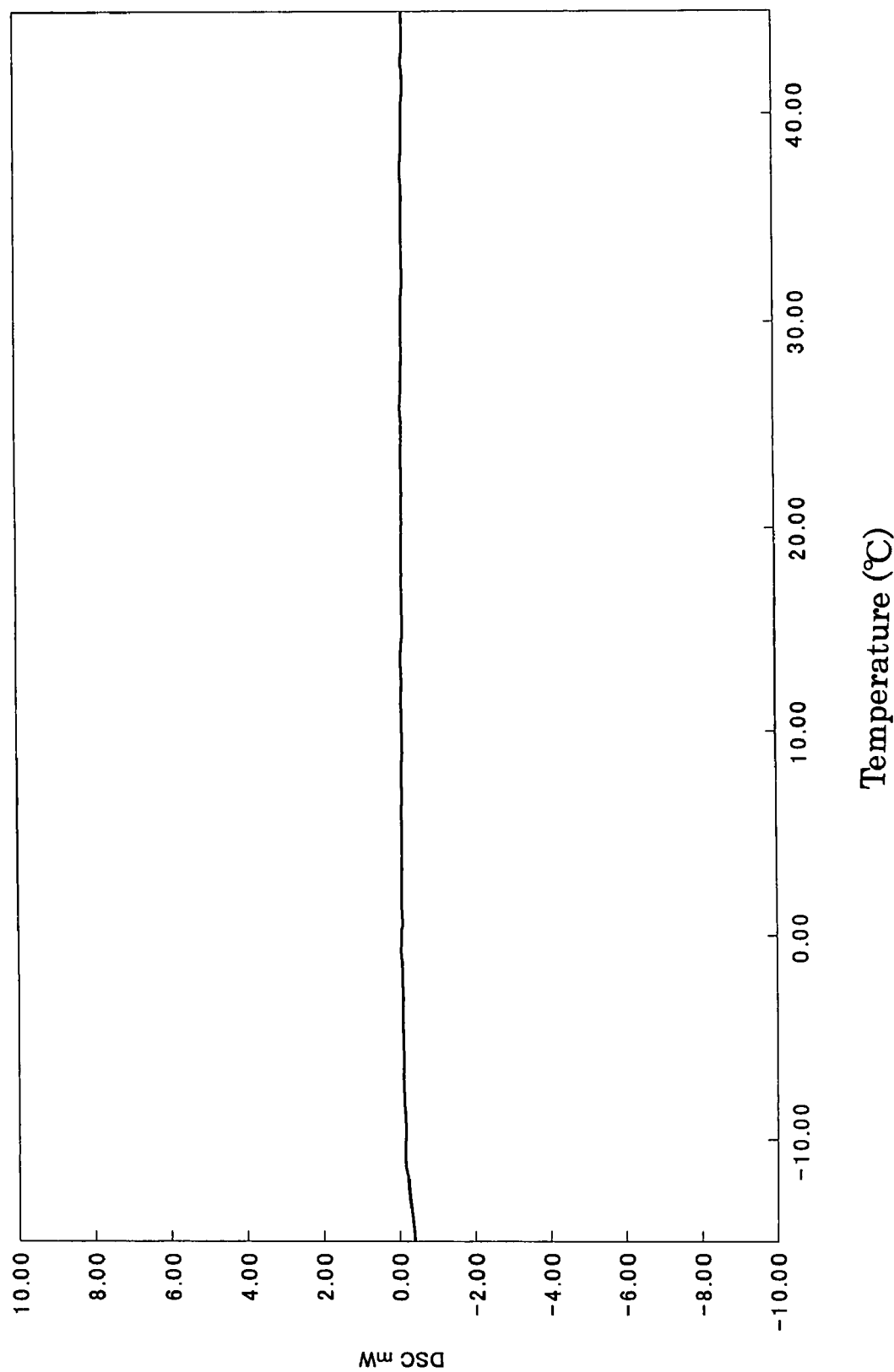
FIG. 1 is a graph showing the results of water-holding property test 2 of the esterification reaction product obtained in Production Example 1.

First, the esterification reaction product according to the present invention will now be described.

The esterification reaction product of the present invention is obtained by esterifying dipentaerythritol and a 12-hydroxystearic acid polymer and has a hydroxyl value of 20 to 70 mg KOH/g and an acid value of 3 mg KOH/g or less.

The dipentaerythritol used for manufacturing the esterification reaction product of the present invention may be a commercially available one. For example, dipentaerythritol available from KOEI PERSTOP Co., Ltd. under the trade name "di-Pentalit" can be used.

The 12-hydroxystearic acid polymer used for manufacturing the esterification reaction product of the present invention is a polymer of 12-hydrocystearic acid having one hydroxyl group in the molecule. For example, the 12-hydrocystearic acid polymer can be obtained by polymerizing 12-hydroxystearic acid given by hydrogenating ricinoleic acid obtained by hydrolysis of castor oil.

The polymerization of 12-hydroxystearic acid is a reaction for esterifying a hydroxyl group or carboxyl group of a 12-hydroxystearic acid molecule with a carboxyl group or hydroxyl group of another 12-hydroxystearic acid molecule, namely, intermolecular esterification.

The polymerization of 12-hydroxystearic acid can be conducted, for example, as follows:

12-Hydroxystearic acid is charged in a reaction vessel and is stirred for esterification reaction (polymerization reaction) at 180 to 220° C. for 5 to 30 hours in the presence or absence of an acid, alkali, or other metal catalyst, preferably, in an organic solvent and/or gas which are inactive to the reaction.

The 12-hydroxystearic acid may be a commercially available one. For example, 12-hydroxystearic acid manufactured by Kokura Synthetic Industies, Ltd. under the trade name "12-Hydro acid (HP)", "Hydroxystearic Acid" manufactured by Kawaken Fine Chemicals Co., Ltd., and "Hydrogenated Castor Oil Fatty Acid" manufactured by NOF Corp. can be used.

12-Hydroxystearic acid polymers having a polymerization degree of 2 to 12 are preferably used for manufacturing the esterification reaction product of the present invention. A 12-hydroxystearic acid polymer having a polymerization degree in this range can improve water-holding properties, dispersibility, adhesion, waterproof-film-forming ability, and non-dyeing properties. The polymerization degree is more preferably 4 to 12, and most preferably 6 to 12. The average polymerization degree can be adjusted within the above-mentioned range by carrying out the polymerization reaction of 12-hydroxystearic acid while measuring acid value of the reaction product. That is, the average polymerization degree can be readily adjusted to the above-mentioned range by sampling a reaction product during the progress of the polymerization reaction of 12-hydroxystearic acid, measuring acid value of the sampled reaction product, calculating average polymerization degree from the acid value, and terminating the esterification reaction (polymerization reaction) at the point that gives the desired average polymerization degree is obtained.

The hydroxyl value of esterification reaction product of the present invention is 20 to 70 mg KOH/g, preferably 20 to 60 mg KOH/g, more preferably 25 to 50 mg KOH/g, and most preferably 30 to 40 mg KOH/g. When the hydroxyl value is lower than 20 mg KOH/g, the desired water-holding properties and dispersibility cannot be achieved. On the contrary, when the hydroxyl value is higher than 70 mg KOH/g, the manufacturing becomes difficult. When the hydroxyl value is lower than 20 mg KOH/g, the manufacturing becomes also difficult. The hydroxyl value of the esterification reaction product can be adjusted to the above-mentioned range by, for example, controlling the ratio of dipentaerythritol or a 12-hydroxystearic acid polymer.

The acid value of the esterification reaction product of the present invention is 3 mg KOH/g or less and preferably 0 to 3 mg KOH/g. When the acid value is higher than 3 mg KOH/g, odor may occur.

The acid value of the esterification reaction product can be adjusted to the above-mentioned range by sampling a reaction product during the progress of the esterification reaction, measuring acid value of the sampled reaction product, and terminating the esterification reaction at the point that gives the desired acid value.

As described above, the esterification reaction product of the present invention is obtained by esterifying dipentaerythritol and a 12-hydroxystearic acid polymer.

The charging amount of the 12-hydroxystearic acid polymer used for esterification reaction is preferably 1 to 6 moles, more preferably 1.5 to 5 moles, and most preferably 2 to 4 moles on the basis of 1 mole of dipentaerythritol for adjusting the hydroxyl value to the above-mentioned range and reducing the amount of unreacted dipentaerythritol.

The appearance, viscosity, and water-holding properties can be provided to the resulting ester composition by thus adjusting the charging ratio.

The esterification of dipentaerythritol and a 12-hydroxystearic acid polymer is specifically conducted as follows: dipentaerythritol and a 12-hydroxystearic acid polymer are put into a reaction vessel and are subjected to esterification in an inactive organic solvent and/or gas at 200 to 220° C. for 1 to 20 hours. Then, the reaction mixture is purified to obtain an esterification reaction product of dipentaerythritol and the 12-hydroxystearic acid polymer.

In the above-mentioned esterification reaction, a catalyst may be used according to need. Examples of the catalyst include acid catalysts and alkoxides of alkaline earth metals. These catalysts are preferably used at an amount of about 0.001 to 1.0% by mass to of the total mass of reaction raw materials.

After the reaction, the catalyst and unreacted raw materials can be removed by conducting known purification treatment such as washing with water, alkali deacidification, or absorptive treatment. In addition, the resulting reactant product can be further purified by conducting bleaching and deodorizing.

Thus, an esterification reaction product can be obtained as a colorless or light yellow transparent odorless liquid. The resulting esterification reaction product can be used as an ingredient of cosmetic products described below.

Next, cosmetic products according to the present invention will be described.

The cosmetic products of the present invention contain the esterification reaction product of the present invention.

The application and formulation of the cosmetic products of the present invention are not especially limited. Examples of the cosmetic products include lip cosmetics, foundation, emollient cream, milky lotion, makeup bases, hair cream, shampoo, hair rinse, hair conditioners, hand cream, serum, eyebrow and eye cosmetics, nail cosmetics, and sunscreen cosmetics.

These cosmetic products can be manufactured by known methods without any particular limitation.

The cosmetic products according to the present invention contain the above-mentioned esterification reaction product. Thereby, adhesion, waterproof-film-forming, pigment-dispersing, and non-dyeing properties are imparted to, in particular, makeup cosmetics among the above-mentioned cosmetic products, e.g., lip cosmetics, makeup bases, foundation, eyebrow and eye cosmetics, and nail cosmetics. In the makeup bases and the foundation (liquid foundation, powder foundation, stick-type foundation, and cream foundation), the waterproof-film-forming ability reduces roughness of skin to allow foundation fit better and also imparts softening and moisturizing effects.

In addition, the cosmetic products according to the present invention are improved in resistance to sebum, perspiration, and rubbing. Thereby, the finish of makeup can last for a long time. Therefore, the present invention can be applied to sunscreen agents. In lip cosmetics (lip rouge, lip gloss, and lip balm), eyebrow and eye cosmetics (eyeliner, mascara, eyeshadow, and eye pencil), and nail cosmetics (nail enamel, base coat, and top coat), uniform cosmetic films can be maintained for a long time by the excellent adhesion properties. In addition, the coloring is improved by the excellent pigment-dispersing properties (coloring agent-dispersing properties). In general, a lip cosmetic product containing a dye may cause troubles (chapping, drying, allergy, darkening, and so on) by dyeing skin or mucous membrane. However, in the lip cosmetic products containing the esterification reaction product of the present invention, the makeup lasts for a long time without dying skin or lip by the dyes contained in the cosmetic products, and smudges of the cosmetic products are less caused. Furthermore, emulsion-type lip cosmetic products can be readily prepared. In addition, effects of moisturizing and conditioning lip can be imparted to cosmetic products by blending a moisturizing agent, an inorganic salt, an organic salt, a water-soluble agent, or an animal or plant extract to the cosmetic products. Similarly, moisturizing effect can be imparted to cake-type and oil-type foundation by blending a moisturizing agent, an inorganic salt, an organic salt, a water-soluble agent, or an animal or plant extract to the foundation. Furthermore, the esterification reaction product of the present invention can be blended to oil phases of oil-in-water-type emulsion cosmetic products.

In particular, sunscreen cosmetic products having a long-acting effect, excellent adhesion to skin, and film-forming feeling can be obtained by blending the esterification reaction product of the present invention thereto. Examples of the formulation of the sunscreen cosmetic include water-in-oil-type (W/O type) sunscreen cream, water-in-oil-type (W/O type) sunscreen milky lotion, water-in-oil-type (W/O type) sunscreen multi-phase emulsion, oil-in-water-type (O/W type) sunscreen cream, and oil-in-water-type (O/W type) sunscreen milky lotion.

In addition, since the esterification reaction product of the present invention is excellent in pigment-dispersing properties, inorganic pigments can be uniformly dispersed in sunscreen cosmetic products by blending the esterification reaction product to the cosmetic products. Therefore, a uniform film of an inorganic pigment is formed on skin by applying the cosmetic product onto the skin, and thereby the ultraviolet preventing effect can be enhanced. In other words, the SPF (Sun Protection Factor) of the cosmetic product can be enhanced by the same amount of the inorganic pigment. Further, the high water-holding properties of the esterification reaction product of the present invention can improve the stability of W/O type emulsions, and thereby water-in-oil-type (W/O type) emulsions excellent in the long-term stability can be obtained by blending the esterification reaction product to the emulsions. Thus, sunscreen cosmetic products having a long-acting effect, excellent adhesion to skin, and film-forming feeling and further having excellent ultraviolet preventing effect and long-term stability can be obtained by blending the above-mentioned ester compound to the sunscreen cosmetic products.

The content of the esterification reaction product of the present invention in a cosmetic product varies depending on the formulation of the cosmetic product, but is preferably 0.1 to 80% by mass, more preferably 1 to 80% by mass, more preferably 1 to 60% by mass, more preferably 1 to 40% by mass, and most preferably 5 to 40% by mass for further improving the feelings of use such as adhesion, waterproof-film-forming, and moisturizing.

The esterification reaction product of the present invention is excellent in the water-holding properties and thereby has an effect of enhancing the stability of W/O emulsion. Therefore, water-in-oil-type (W/O type) emulsion having long-term stability can be obtained by blending the esterification reaction product to the emulsion. In particular, the effect can be further enhanced by adding an organic modified clay mineral to the emulsion. Such water-in-oil-type (W/O type) emulsion includes, for example, (a) an esterification reaction product, (b) an organic modified clay mineral, (c) oil, and (d) water. The contents of the respective ingredients of such emulsion are preferably (a) 1 to 30% by mass, (b) 0.01 to 10% by mass, (c) 10 to 80% by mass, and (d) 10 to 80% by mass, and more preferably (a) 1 to 20% by mass, (b) 0.1 to 5% by mass, (c) 15 to 80% by mass, and (d) 20 to 80% by mass to the total amount of the emulsion. This water-in-oil type (W/O type) emulsion can be widely applied to emulsion cosmetic products such as cream, milky lotion, and aerosol, and is particularly suitable for sunscreen cosmetics and moisturizing cream.

The cosmetic products according to the present invention may contain various ingredients generally used in cosmetic products, according to need, in the range that does not impair the effects of the present invention.

Such ingredients are properly selected based on use and formulation of the cosmetic product, and examples of the ingredients include oil ingredients, aqueous ingredients, polymer emulsions, anionic surfactants, cationic surfactants, amphoteric surfactants, oleophilic nonionic surfactants, hydrophilic nonionic surfactants, natural surfactants, moisturizing agents, thickeners, preservatives, powdery ingredients, pigments, pH-adjusters, antioxidants, ultraviolet absorbers, perfumes, dyes, sequestering agents, and purified water.

Examples of the oil ingredients include carbon hydrides such as liquid paraffin, heavy liquid isoparaffin, solid paraffin, α-olefin oligomer, squalane, Vaseline, polyisobutylene, polybutene, montan wax, ceresin wax, microcrystalline wax, polyethylene wax, and Fisher-Tropsch wax; fats and oils such as olive oil, castor oil, jojoba oil, mink oil, and macademia nut oil; waxes such as beeswax, candelilla wax, spermaceti wax, candellila wax, carnauba wax, and Japan wax; esters such as cetyl 2-ethylhexanoate, cetyl isooctanoate, isopropyl myristate, isopropyl palmitate, octyldodecyl myristate, polyglyceryl diisostearate, polyglyceryl triisostearate, diglyceryl triisostearate, polyglyceryl tetraisostearate, diglyceryl tetraisostearate, trioctanoin, diisostearyl malate, neopentyl glycol dioctanoate, propylene glycol didecanoate, cholesterol fatty acid ester, isopropyl myristate, glyceryl monostearate, glycerin fatty acid ester eicosadioate condensate, dextrin palmitate, dextrin myristate, and dextrin fatty acid ester; fatty acids such as stearic acid, lauric acid, myristic acid, behenic acid, isostearic acid, and oleic acid; higher alcohols such as stearyl alcohol, cetyl alcohol, lauryl alcohol, oleyl alcohol, isostearyl alcohol, behenyl alcohol, stearyl alcohol, octyldodecanol, and isohexadecyl alcohol; silicones such as low-polymerized dimethylpolysiloxane, high-polymerized dimethylpolysiloxane, methylphenylpolysiloxane, decamethylcyclopentasiloxane, octamethylcyclotetrasiloxane, polyether-modified polysiloxane, polyoxyalkylene/alkylmethylpolysiloxane/methylpolysiloxane copolymer, and alkoxy-modified polysiloxane; fluorinated oils such as perfluorodecane, perfluorooctane, and perfluoropolyether; amino acid ester oils such as N-acylglutamic acid such as stearoylglutamic acid, and di(cholesteryl or phytosterol/behenyl/octyldodecyl) N-lauroyl-L-glutamate; and lanolin derivatives such as lanolin, liquid lanolin, lanolin acetate, liquid lanolin acetate, isopropyl lanolate, and lanolin alcohol. These oil ingredients may be used alone or in a combination of two or more thereof.

Examples of the aqueous ingredients include lower alcohols such as ethyl alcohol and butyl alcohol; glycols such as propylene glycol, 1,3-butylene glycol, dipropylene glycol, and polyethylene glycol; glycerols such as glycerin, diglycerin, and polyglycerin; and plant extracts such as aloe vera, witch hazel, hammamelis, cucumber, tomato, apple, lemon, lavender, and rose. These aqueous ingredients may be used alone or in a combination of two or more thereof.

Examples of the polymer emulsions include alkyl acrylate copolymer emulsion, alkyl methacrylate polymer emulsion, alkyl acrylate copolymer emulsion, alkyl methacrylate copolymer emulsion, acrylic acid/alkyl acrylate copolymer emulsion, methacrylic acid/alkyl methacrylate copolymer emulsion, alkyl acrylate/styrene polymer emulsion, alkyl methacrylate/styrene copolymer emulsion, vinyl acetate polymer emulsion, polyvinyl acetate emulsion, vinyl acetate-containing copolymer emulsion, vinylpyrrolidone/styrene copolymer emulsion, and silicone-containing copolymer emulsion. These polymer emulsions may be used alone or in a combination of two or more thereof.

Examples of the anionic surfactants include soap base materials; fatty acid soap such as sodium laurate and sodium palmitate; higher alkyl sulfate esters such as sodium lauryl sulfate and potassium lauryl sulfate; alkyl ether sulfate esters such as triethanolamine polyoxyethylene (POE) laurylether sulfate and sodium POE laurylether sulfate; N-acylsarcosinates such as sodium lauroylsarcosinate; higher fatty acid amide sulfonates such as sodium N-myristoyl-N-methyl taurate, sodium coconut fatty acid methyl taurate, and sodium lauryl methyl taurate; phosphate esters such as sodium POE oleylether phosphate and POE stearylether phosphate; sulfosuccinates such as di-2-ethylhexyl sodium sulfosuccinate, sodium monolauroyl monoethanolamide polyoxyethylene sulfosuccinate, and sodium lauryl polypropylene glycol sulfosuccinate; alkylbenzenesulfonates such as sodium linear dodecylbenzene sulfonate, triethanolamine linear dodecylbenzene sulfonate, and linear dodecylbenzenesulfonic acid; N-acylglutamates such as monosodium N-lauroyl glutamate, disodium N-stearoyl glutamate, and monosodium N-myristoyl-L-glutamate; higher fatty acid ester sulfate esters such as sodium hydrogenated coconut fatty acid glyceryl sulfate; sulfated oils such as Turkey red oil; POE alkyl ether carboxylates; POE alkylallyl ether carboxylate; α-olefin sulfonates; higher fatty acid ester sulfonates; secondary alcohol sulfate esters; higher fatty acid alkylolamide sulfate esters; sodium lauroyl monoethanolamide succinate; di-triethanolamine N-palmitoylaspartate; and sodium caseinate. These anionic surfactants may be used alone or in a combination of two or more thereof.

Examples of the cationic surfactants include alkyltrimethylammonium salts such as stearyltrimethylammonium chloride and lauryltrimethylammonium chloride; dialkyldimethylammonium salts such as distearyldimethylammonium chloride; alkylpyridinium salts such as poly(N,N'-dimethyl-3,5-methylenepiperidinium)chloride and cetylpyridinium chloride; alkyl quaternary ammonium salts; alkyldimethylbenzylammonium salts; alkylisoquinolinium salts; dialkylmorpholinium salts; POE alkylamines; alkylamine salts; polyamine fatty acid derivatives; amyl alcohol fatty acid derivatives; benzalkonium chloride; and benzethonium chloride. These cationic surfactants may be used alone or in a combination of two or more thereof.

Examples of the amphoteric surfactants include imidazoline amphoteric surfactants such as sodium 2-undecyl-N,N,N-(hydroxyethylcarboxymethyl)-2-imidazoline and 2-cocoyl-2-imidazoliniumhydroxide-1-carboxyethyloxy 2 sodium salt; and betaine surfactants such as 2-heptadecyl-N-carboxymethyl-N-hydroxyethylimidazolinium betaine, lauryldimethylaminoacetic acid betaine, alkylbetaine, amidobetaine, and sulfobetaine. These amphoteric surfactants may be used alone or in a combination of two or more thereof.

Examples of the oleophilic nonionic surfactants include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexylate, and diglycerolsorbitan tetra-2-ethylhexylate; sucrose fatty acid esters; glyceryl fatty acids such as glyceryl monocottonseed fatty acid, glyceryl monoerucate, glyceryl sesquioleate, glyceryl monostearate, glyceryl α,α'-oleate pyroglutamate, and glyceryl monostearate; polyglyceryl fatty acid esters such as diglyceryl monoisostearate and diglyceryl diisostearate; propylene glycol fatty acid esters such as propylene glycol monostearate; hydrogenated castor oil derivatives; and glycerin alkylethers. These oleophilic nonionic surfactants may be used alone or in a combination of two or more thereof.

Examples of the hydrophilic nonionic surfactants include POE-sorbitan fatty acid esters such as POE-sorbitan monooleate, POE-sorbitan monostearate, POE-sorbitan monoolate, and POE-sorbitan tetraoleate; POE-sorbitol fatty acid esters such as POE-sorbitol monolaurate, POE-sorbitol monooleate, POE-sorbitol pentaoleate, and POE-sorbitol monostearate; POE-glycerin fatty acid esters such as POE-glycerin monostearate, POE-glycerin monoisostearate, and POE-glycerin triisostearate; POE-fatty acid esters such as POE-monooleate, POE-distearate, POE-monodioleate, and ethylene glycol distearate; POE-alkyl ethers such as POE-lauryl ether, POE-oleyl ether, POE-stearyl ether, POE-behenyl ether, POE-2-octyldodecyl ether, and POE-cholestanol ether; pluronic types such as Pluronic; POE/POP alkyl ethers such as POE/POP-cetyl ether, POE/POP-2-decyltetradecyl ether, POE/POP-monobutyl ether, POE/POP-hydrogenated lanolin, and POE/POP-glycerin ether; tetra POE/tetra POP-ethylenediamine polymers such as Tetronic; POE-castor oil hydrogenated castor oil derivatives such as POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, and POE-hydrogenated castor oil maleate; POE-beeswax/lanolin derivatives such as POE-sorbitol beeswax; alkanol amides such as coconut oil fatty acid diethanolamide, lauric acid monoethanolamide, and fatty acid isopropanolamide; POE-propylene glycol fatty acid esters; POE-alkylamines; POE-fatty acid amides; sucrose fatty acid esters; POE-nonylphenyl formaldehyde polymers; alkylethoxydimethylamine oxides; and trioleyl phosphate. These hydrophilic nonionic surfactants may be used alone or in a combination of two or more thereof.

Examples of the natural surfactants include lecithins such as soybean phospholipid, hydrogenated soybean phospholipid, yolk phospholipid, and hydrogenated yolk phospholipid; and soybean saponin. These natural surfactants may be used alone or in a combination of two or more thereof.

Examples of the moisturizing agents include polyethylene glycol, propylene glycol, glycerin, 1,3-butylene glycol, xylitol, sorbitol, maltitol, chondroitin sulfuric acid, hyaluronic acid, mucoitin sulfuric acid, caronic acid, atherocollagen, cholesteryl-12-hydroxystearate, sodium lactate, urea, bile acid salts, dl-pyrrolidone carboxylic acid salts, short-chain soluble collagen, diglycerol (EO) PO adducts, Rosa roxburghii extracts, Achillea millefolium extracts, and Melilotus officinalis extracts. These moisturizing agents may be used alone or in a combination of two or more thereof.

Examples of the thickeners include gum Arabic, carrageenan, karaya gum, tragacanth gum, carob gum, quince seeds (marmelo), casein, dextrin, gelatin, sodium pectate, sodium alginate, methylcellulose, ethylcellulose, CMC, hydroxyethylcellulose, hydroxypropylcellulose, PVA, PVM, PVP, sodium polyacrylate, carboxyvinyl polymer, locust bean gum, guar gum, tamarind gum, dialkyldimethylammonium cellulose sulfate, xanthan gum, magnesium aluminum silicate, bentonite, hectorite, quaternary ammonium cation-modified bentonite, quaternary ammonium cation-modified hectorite, and decaglycerin fatty acid ester eicosadioate condensate. These thickeners may be used alone or in a combination of two or more thereof.

Examples of the preservatives include methylparaben, ethylparaben, and butylparaben. These preservatives may be used alone or in a combination of two or more thereof.

Examples of the powdery ingredients include inorganic powder such as talc, kaolin, mica, sericite, white mica, gold mica, synthetic mica, red mica, black mica, rithia mica, vermicurite, magnesium carbonate, calcium carbonate, aluminum silicate, barium silicate, calcium silicate, magnesium silicate, strontium silicate, tungstate metal salts, magnesium, silica, zeolite, barium sulfate, calcined calcium sulfate (calcined gypsum), calcium phosphate, fluorine apatite, hydroxyapatite, ceramic powder, metallic soap (zinc myristate, calcium palmitate, and aluminum stearate), and boron nitride; organic powder such as polyamide resin powder (nylon powder), polyethylene powder, methyl polymethacrylate powder, polystyrene powder, copolymer resin powder of styrene and acrylic acid, benzoguanamine resin powder, poly(ethylene tetrafluoride) powder, and cellulose powder. These powder ingredients may be used alone or in a combination of two or more thereof.

Examples of the pigments include inorganic white pigments such as titanium dioxide and zinc oxide (including fine particles of titanium dioxide or zinc oxide which are used as ultraviolet-scattering agents and surface-coated inorganic white pigments given by coating the surfaces of the particles with fatty acid soap such as aluminum stearate or zinc palmitate; fatty acid such as stearic acid, myristic acid, or palmitic acid; or fatty acid ester such as dextrin palmitate); inorganic red pigments such as iron oxide (bengara) and iron titanate; inorganic brown pigments such as γ-iron oxide; inorganic yellow pigments such as yellow iron oxide and yellow ocher; inorganic black pigments such as black iron oxide, carbon black, and titanium suboxide; inorganic violet pigments such as mango violet and cobalt violet; inorganic green pigments such as chromium oxide, chromium hydroxide, and cobalt titanate; inorganic blue pigments such as ultramarine blue and iron blue; pearl pigments such as titanium oxide-coated mica, titanium oxide-coated bismuth oxychloride, titanium oxide-coated talc, colored titanium oxide-coated mica, bismuth oxychloride, and argentine film; metal powder pigments such as aluminum powder and copper powder; organic pigments such as Red Nos. 201, 202, 204, 205, 220, 226, 228, and 405, Orange Nos. 203 and 204, Yellow Nos. 205 and 401, and Blue No. 404; and organic pigments such as zirconium, barium, and aluminum lakes of Red Nos. 3, 104, 106, 227, 230, 401, and 505, Orange No. 205, Yellow Nos. 4, 5, 202, and 203, Green No. 3, and Blue No. 1. These pigments may be used alone or in a combination of two or more thereof.

Examples of the pH-adjusters include edetic acid, disodium edetate, citric acid, sodium citrate, sodium hydroxide, potassium hydroxide, and triethanolamine. These pH-adjusters may be used alone or in a combination of two or more thereof.

Examples of the antioxidants include vitamin C, its derivatives, and salts thereof; tocopherol, its derivatives, and salts thereof; dibutylhydroxy toluene; butylhydroxy anisole; and gallic acid ester. These antioxidants may be used alone or in a combination of two or more thereof.

Examples of the ultraviolet absorbers include benzoate ultraviolet absorbers such as p-aminobenzoic acid (hereinafter referred to as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA octyl ester; anthranilic acid ultraviolet absorbers such as homomethyl-N-acetyl anthranilate; salicylic acid ultraviolet absorbers such as amyl salicylate, menthyl salicylate, homomethyl salicylate, octyl salicylate, phenyl salicylate, benzyl salicylate, and p-isopropanol phenyl salicylate; cinnamic acid ultraviolet absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glycerylmono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; urocanic acid; ethyl urocanate ester; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzalazine; dianisoylmethane; 4-methoxy-4'-t-butyldibenzoylmethane; 5-(3,3-dimethyl-2-norbornylidene)-3-pentan-2-one; 2,4,6-trianilino-p-(carbo-2'-ethylhexyl-1'-oxy)1,3,5-triazine; and 4-tert-butyl-4'-methoxydibenzoylmethane. These ultraviolet absorbers may be used alone or in a combination of two or more thereof.

Examples of the dyes include chlorophyll and β-carotene. These dyes may be used alone or in a combination of two or more thereof.

Examples of the perfumes include plant perfumes such as rose oil, jasmine oil, and lavender oil; and synthetic perfumes such as limonene, citral, linalool, and eugenol. These perfumes may be used alone or in a combination of two or more thereof.

Examples of the sequestering agents include disodium edetate, edetic acid salts, and hydroxyethane diphosphonate. These sequestering agents may be used alone or in a combination of two or more thereof.

EXAMPLES

The present invention will now be further described in detail with reference to Examples. However, it is apparent that the present invention is not limited to the Examples. In the following Examples, the terms part(s) and % denote part(s) by mass and % by mass, respectively, unless otherwise specified.

Further, the acid value and hydroxyl value of esterification reaction products were measured according to an old edition of the Japanese Standards of Cosmetic Ingredients.

Production Example 1

A 1 liter tetra-neck flask equipped with a stirrer, a temperature gauge, a nitrogen gas inlet tube, and a moisture separator was charged with 483 g of 12-hydroxystearic acid (manufactured by Kawaken Fine Chemicals Co., Ltd. under the trade name Hydroxystearic Acid), and tin chloride as a catalyst at a concentration of 0.1% to the total charged amount and xylol as a reflux solvent at a concentration of 5% to the total charged amount were added thereto. The resulting mixture was heated to 200° C. for 15 hours while removing produced water under a nitrogen gas flow to obtain a 12-hydroxystearic acid polymer. The obtained polymer had an acid value of 33 mg KOH/g. The average polymerization degree calculated from the acid value was 6 to confirm that the obtained product was a hexamer of 12-hydroxystearic acid.

Then, a 1 liter tetra-neck flask equipped with a stirrer, a temperature gauge, a nitrogen gas inlet tube, and a moisture separator was charged with 477 g of the thus obtained 12-hydroxystearic acid polymer (acid value: 33 mg KOH/g, hexamer) and 17 g of dipentaerythritol (manufactured by KOEI PERSTOP Co., Ltd. under the trade name "di-Pentalit"). The resulting mixture was subjected to reaction at 210° C. while removing produced water under a nitrogen gas flow until the acid value of the product was reduced to 1 mg KOH/g or less.

After the completion of the reaction, the catalyst was removed by filtration. Then, the reaction product was bleached with activated clay and deodorized by blowing steam under reduced pressure to obtain 340 g of an esterification reaction product as a viscous liquid at room temperature. The obtained esterification reaction product had an acid value of 0.5 mg KOH/g and a hydroxyl value of 35 mg KOH/g.

Production Example 2

A 12-hydroxystearic acid polyer was obtained by the same procedure as in Production Example 1, except that 487 g of 12-hydroxystearic acid, manufactured by Kokura Synthetic Industries, Ltd. under the trade name "12-Hydro acid (HP)", was used and the reaction was conducted for 18 hours. The obtained polymer was measured for its acid value. The acid value was 19 mg KOH/g, and the average polymerization degree calculated from the acid value was 10 to confirm that the obtained product was a decamer.

Then, 344 g of an esterification reaction product was obtained by the same procedure as in Production Example 1, except that 478 g of the thus obtained 12-hydroxystearic acid polymer (acid value: 19 mg KOH/g, decamer) and 13 g of dipentaerythritol were used. The obtained esterification reaction product had an acid value of 0.2 mg KOH/g and a hydroxyl value of 31 mg KOH/g.

Production Example 3

A 1 liter tetra-neck flask equipped with a stirrer, a temperature gauge, a nitrogen gas inlet tube, and a moisture separator was charged with 413 g of 12-hydroxystearic acid (manufactured by Kawaken Fine Chemicals Co., Ltd. under the trade name Hydroxystearic Acid) and 87 g of dipentaerythritol (manufactured by KOEI PERSTOP Co., Ltd. under the trade name "di-Pentalit"), and tin chloride as a catalyst at a concentration of 0.1% to the total charged amount and xylol as a reflux solvent at a concentration of 5% to the total charged amount were added thereto. The resulting mixture was subjected to reaction at 210° C. for 20 hours while removing produced water under a nitrogen gas flow.

After the completion of the reaction, the catalyst was removed by filtration. Then, the reaction product was bleached with activated clay and deodorized by blowing steam under reduced pressure to obtain 325 g of an esterification reaction product as a semisolid (paste) at room temperature.

The obtained esterification reaction product had an acid value of 1.2 mg KOH/g and a hydroxyl value of 123 mg KOH/g.

Production Example 4

A 1 liter tetra-neck flask equipped with a stirrer, a temperature gauge, a nitrogen gas inlet tube, and a moisture separator was charged with 442 g of a 12-hydroxystearic acid polymer (acid value: 33 mg KOH/g, hexamer) prepared by the same procedure as in Production Example 1 and 43 g of dipentaerythritol (manufactured by KOEI PERSTOP Co., Ltd. under the trade name "di-Pentalit"). The resulting mixture was subjected to reaction at 210° C. while removing produced water under a nitrogen gas flow until the acid value of the product was reduced to 1 mg KOH/g or less.

After the completion of the reaction, the product was separated from the unreacted dipentaerythritol, and a target esterification reaction product having a hydroxyl value of about 100 mg KOH/g was not obtained.

Production Example 5

An esterification reaction product (330 g), which was a viscous liquid at room temperature, was obtained by the same procedure as in Production Example 1, except that the amount of the 12-hydroxystearic acid polymer (acid value: 33 mg KOH/g, hexamer) obtained by the same procedure as in Production Example 1 was 462 g and the amount of dipentaerythritol (manufactured by KOEI PERSTOP Co., Ltd. under the trade name "di-Pentalit") was 29 g. The obtained esterification reaction product had an acid value of 0.4 mg KOH/g and a hydroxyl value of 44 mg KOH/g.

Production Example 6

A 12-hydroxystearic acid polymer (acid value: 33 mg KOH/g, hexamer) was obtained by the same procedure as in Production Example 1, except that 12-hydroxystearic acid manufactured by Kokura Synthetic Industries, Ltd., under the trade name "12-Hydro acid (HP)" was used instead of 12-hydroxystearic acid (manufactured by Kawaken Fine Chemicals Co., Ltd. under the trade name Hydroxystearic Acid).

Then, 338 g of an esterification reaction product, which was a viscous liquid at room temperature, was obtained by the same procedure as in Production Example 1, except that the amount of the obtained 12-hydroxystearic acid polymer was 475 g and that the amount of dipentaerythritol (manufactured by KOEI PERSTOP Co., Ltd. under the trade name "di-Pentalit") was 16 g. The obtained esterification reaction product had an acid value of 0.9 mg KOH/g and a hydroxyl value of 52 mg KOH/g.

The esterification reaction products obtained in Production Examples 1 to 3 were evaluated as described below. Table 1 shows the results of evaluations (1), (3), and (4), Table 2 shows the results of evaluations (5) and (6), FIGS. 1 to 6 show the results of evaluation (2), and FIG. 7 shows the results of evaluation (7). In addition, by way of comparison, evaluations (1) to (4) were conducted using liquid lanolin, cholesteryl hydroxystearate (manufactured by The Nisshin OilliO Group, Ltd. under the trade name Salacos HS), or diisostearyl malate (manufactured by The Nisshin OilliO Group, Ltd. under the trade name Cosmol 222). Furthermore, by way of comparison, evaluations (5) and (6) were conducted using liquid lanolin, polyglyceryl triisostearate (manufactured by The Nisshin OilliO Group, Ltd. under the trade name: Cosmol 43V), or diisostearyl malate (manufactured by The Nisshin OilliO Group, Ltd. under the trade name Cosmol 222). Furthermore, by way of comparison, evaluation (7) was conducted using liquid lanolin, trioctanoin (manufactured by The Nisshin OilliO Group, Ltd. under the trade name T.I.O), polyglyceryl triisostearate (manufactured by The Nisshin OilliO Group, Ltd. under the trade name Cosmol 43V), or diisostearyl malate (manufactured by The Nisshin OilliO Group, Ltd. under the trade name Cosmol 222).

(1) Water-Holding Property Test 1

The water-holding property test of esterification reaction products is conducted with reference to the lanolin water retention value test in British Pharmacopoeia (BP) as follows:

A measurement sample (1 g) and Vaseline (9 g) are mixed and vigorously stirred (200 to 300 rpm) in a thermostat chamber at 40° C. while dropwise adding purified water thereto. The point when water is no longer being received is determined as the end-point and is expressed as a percentage of mass of water to mass of the mixture. A higher value means better water-holding properties of the sample.

(2) Water-Holding Property Test 2

A measurement sample and water are mixed at a mass ratio of 7:3 and are vigorously stirred (500 rpm, 3 minutes) in a thermostatic chamber at 70° C. to obtain a water-holding substance. The obtained water-holding substance is analyzed with a differential scanning calorimeter (device name "DSC 6200", manufactured by Seiko Instruments Inc.). That is, the temperature of the water-holding substance is raised at a rate of 2° C./min in the range from −15° C. to 45° C. to obtain a differential scanning calorimetry curve, and the curve is confirmed whether an endothermic peak due to water at around 0° C. is present or not. When this endothermic peak is not observed, the water-holding properties are judged to be good.

(3) Water-Retaining Property Test

A measurement sample (1 g) and Vaseline (9 g) are mixed and vigorously stirred (500 rpm, 3 minutes) in a thermostat chamber at 40° C. while dropwise adding 10 g of purified water thereto (the ratio of purified water to the mixture of sample and Vaseline was 1:1). When the sample become smooth, 10 g of the sample is uniformly applied onto a Petri dish so as to have a thickness of 0.5 to 1.5 mm and then put in a thermostat chamber at 40° C. with the lid off. After 24 hours, the sample is taken out from the chamber. The mass after the still standing is measured, and the reduced mass after the standing is calculated and is expressed as a percentage to the mass of the applied sample. A lower value means better water-retaining properties of the sample.

(4) Dispersibility Test

A sample (4 g) and titanium oxide (20 g) are mixed, and then octyl palmitate (manufactured by The Nisshin OilliO Group, Ltd. under the trade name Salacos P-8) is gradually added thereto. The point when the mixture become uniform as a whole is determined as the wetting point, and the point when the mixture starts to flow by tilting the whole mixture is determined as the fluid point. The amounts of octyl palmitate added until to reach the respective points are measured and used as the wetting point value and the fluid point value.

A lower wetting point value or a smaller difference between the wetting point value and the fluid point value means higher pigment-dispersing properties of the sample.

(5) Non-Dyeing Property Test

A dye (Red No. 218) is dissolved in a sample to prepare a dye mixture containing 0.5% by mass of the dye. This dye mixture is applied to the upper arm of a subject. After 3 hours, the applied dye is wiped away with cotton. The skin is observed under a microscope (×100) for observing the amount of the dye remaining on the skin.

The portion of skin applied with the dye is observed under a microscope (×100), and the samples are classified into the following levels according to visual observation.

◯: skin is not dyed with dye

Δ: skin is slightly dyed with dye

X: skin is dyed with dye

In this evaluation, a smaller amount of the dye remaining on the skin means better non-dyeing properties.

(6) Water Resistant Ability (Waterproof-Film-Forming Ability)

A sample is dissolved in chloroform to prepare a sample solution containing 10% by mass of the sample. The prepared sample solution is applied onto a washed glass plate. Then, the solvent is removed to form a film, and one drop of distilled water is dropped onto the formed film. The contact angle between the film surface and the water droplet is measured. After the measurement, the film is washed with flowing tap water (25 mL/s, 1 minute). The water resistant ability is evaluated by comparing the contact angles before and after the washing. A smaller difference in the contact angle before and after the washing means better water resistant ability.

(7) Oxidative Stability (CDM Test)

A sample is subjected to a CDM test (Standard oils and fats analyzing test method: 120° C., Air: 20 L/hr) to evaluate the oxidative stability. In the test, changes of the dielectric constants are measured over time using a Rancimat type device (manufactured by Metrohm). In the CDM test, a sample exhibiting less increase in the dielectric constant with the lapse of time means to be excellent in oxidative stability.

TABLE 1

| | (1) Water-holding properties (% by mass) | (3) Water-retaining properties (% by mass) | (4) Dispersibility Wetting point (% by mass) | (4) Dispersibility Fluid point (% by mass) |
|---|---|---|---|---|
| Production Example 1 | 740 | 0.8 | 1 | 2 |
| Production Example 2 | 580 | 0.9 | 1 | 2 |
| Production Example 3 | 150 | 8.2 | 2 | 5 |
| Liquid lanolin | 350 | 2.1 | 3 | 5 |
| Cholesteryl hydroxystearate | 320 | 1.9 | 2 | 9 |
| Diisostearyl malate | 200 | 3.0 | 3 | 22 |

The followings were confirmed by the results shown in Table 1. Liquid lanolin, cholesteryl hydroxystearate, and diisostearyl malate were not excellent in water-holding properties, water-retaining properties, and dispersibility. The esterification reaction product prepared in Production Example 3, which did not contain 12-hydroxystearic acid polymers and had a hydroxyl value outside the range of esterification reaction products according of the present invention, was inferior in water-holding properties, water-retaining properties, and dispersibility. On the other hand, the esterification reaction products prepared in Production Examples 1 and 2 were excellent in the water-holding properties, water-retaining properties, and dispersibility.

The results of water-holding test 2 are shown in FIGS. 1 to 6. FIG. 1 is a graph showing the results of water-holding property test 2 of the esterification reaction product obtained in Production Example 1. As shown in FIG. 1, in the esterification reaction product prepared in Production Example 1, an endothermic peak due to water at around 0° C. was not detected. This means that the esterification reaction product prepared in Production Example 1 has an ability to hold a large amount of water as fine particles and is also stable against temperature change.

Figure 2:
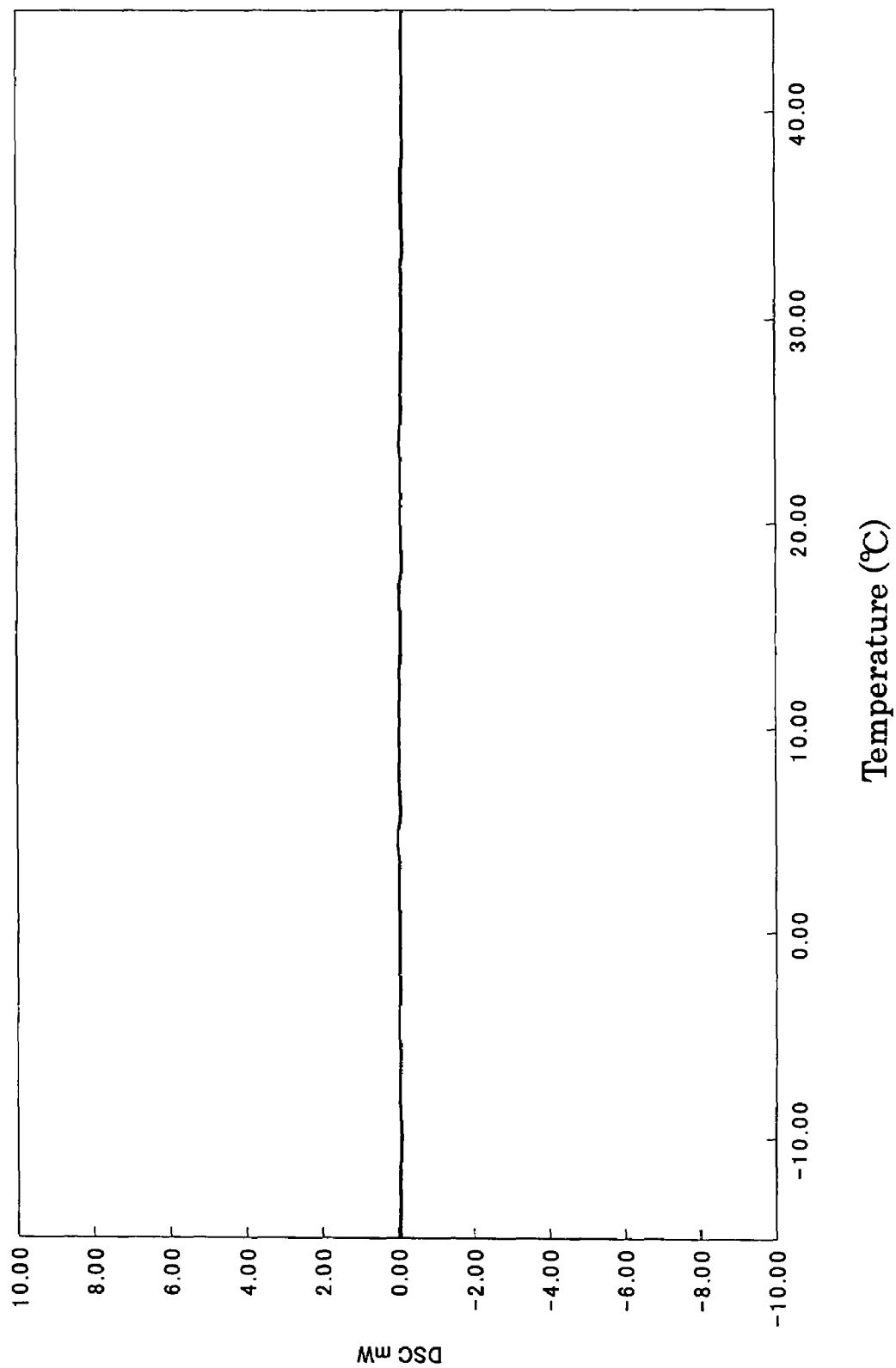
FIG. 2 is a graph showing the results of water-holding property test 2 of the esterification reaction product obtained in Production Example 2.

FIG. 2 is a graph showing the results of water-holding property test 2 of the esterification reaction product obtained in Production Example 2. As shown in FIG. 2, in the esterification reaction product prepared in Production Example 2, an endothermic peak due to water at around 0° C. was not detected. This means that the esterification reaction product prepared in Production Example 2 has an ability to hold a large amount of water as fine particles and is also stable against temperature change.

Figure 3:
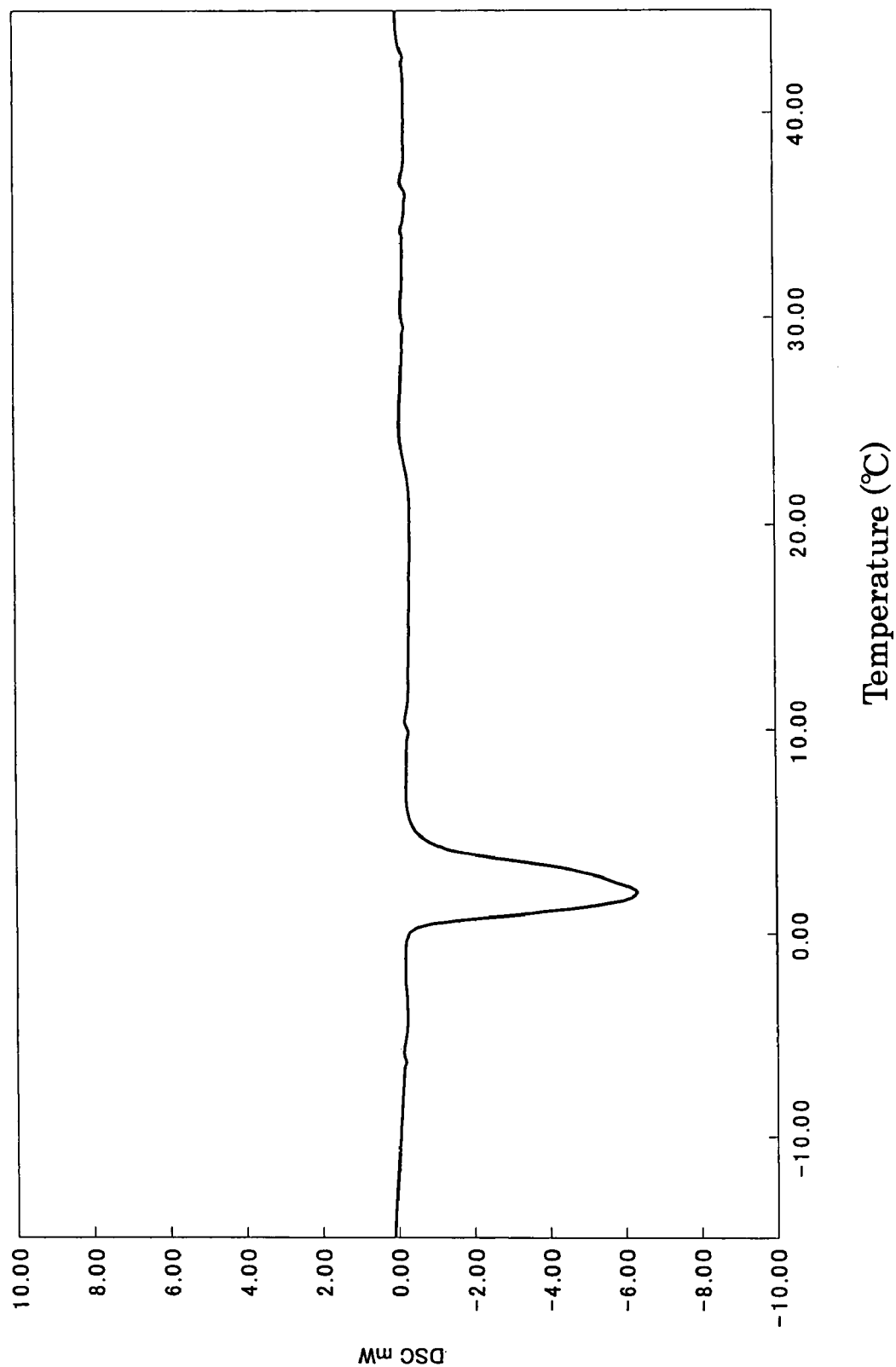
FIG. 3 is a graph showing the results of water-holding property test 2 of the esterification reaction product obtained in Production Example 3.

FIG. 3 is a graph showing the results of water-holding property test 2 of the esterification reaction product obtained in Production Example 3. As shown in FIG. 3, in the esterification reaction product prepared in Production Example 3, an endothermic peak due to water at around 0° C. was detected. This means that the esterification reaction product prepared in Production Example 3 does not have an ability to hold a large amount of water as fine particles and is also not stable against temperature change.

Figure 4:
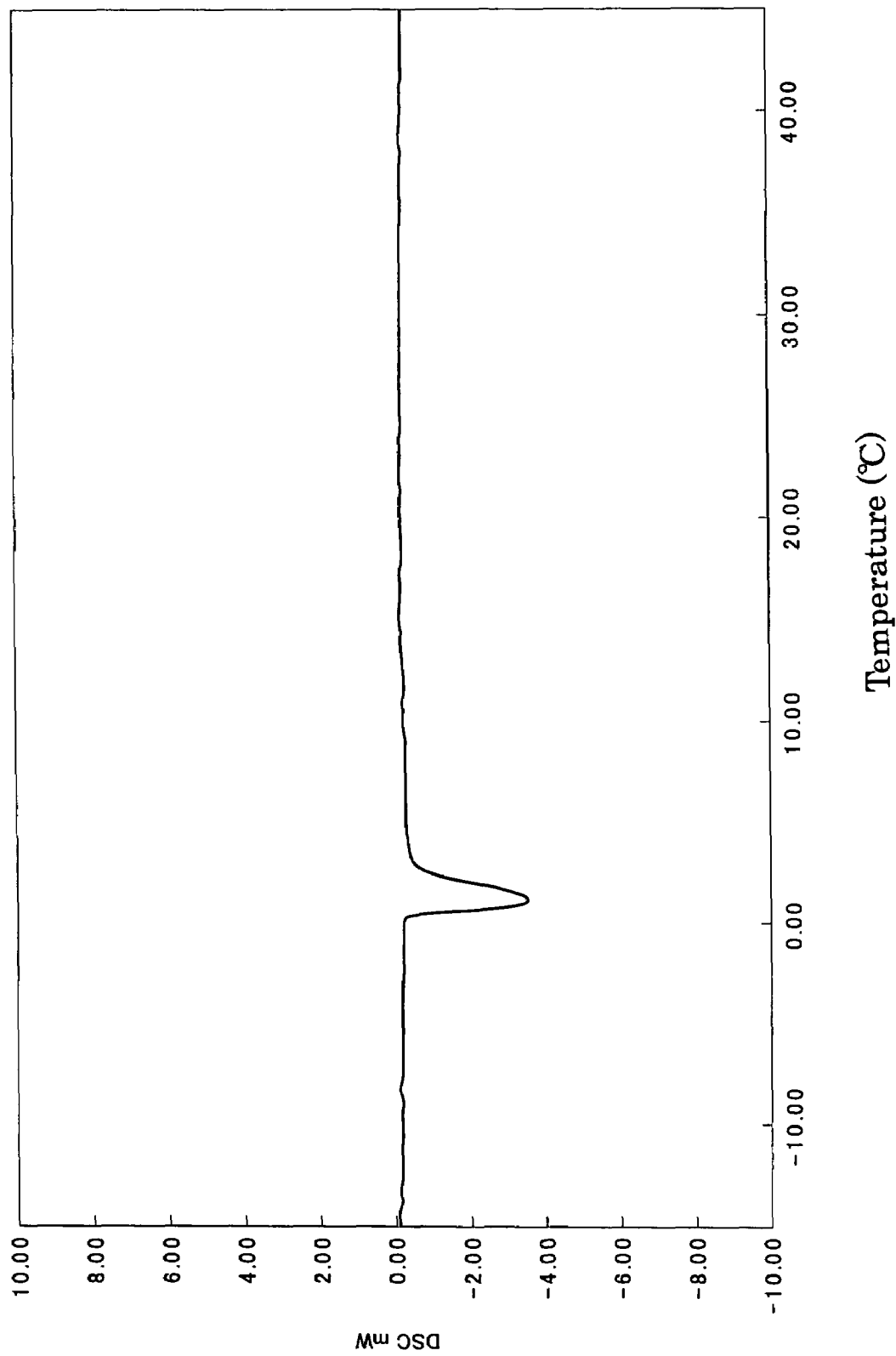
FIG. 4 is a graph showing the results of water-holding property test 2 of liquid lanolin.
Figure 5:
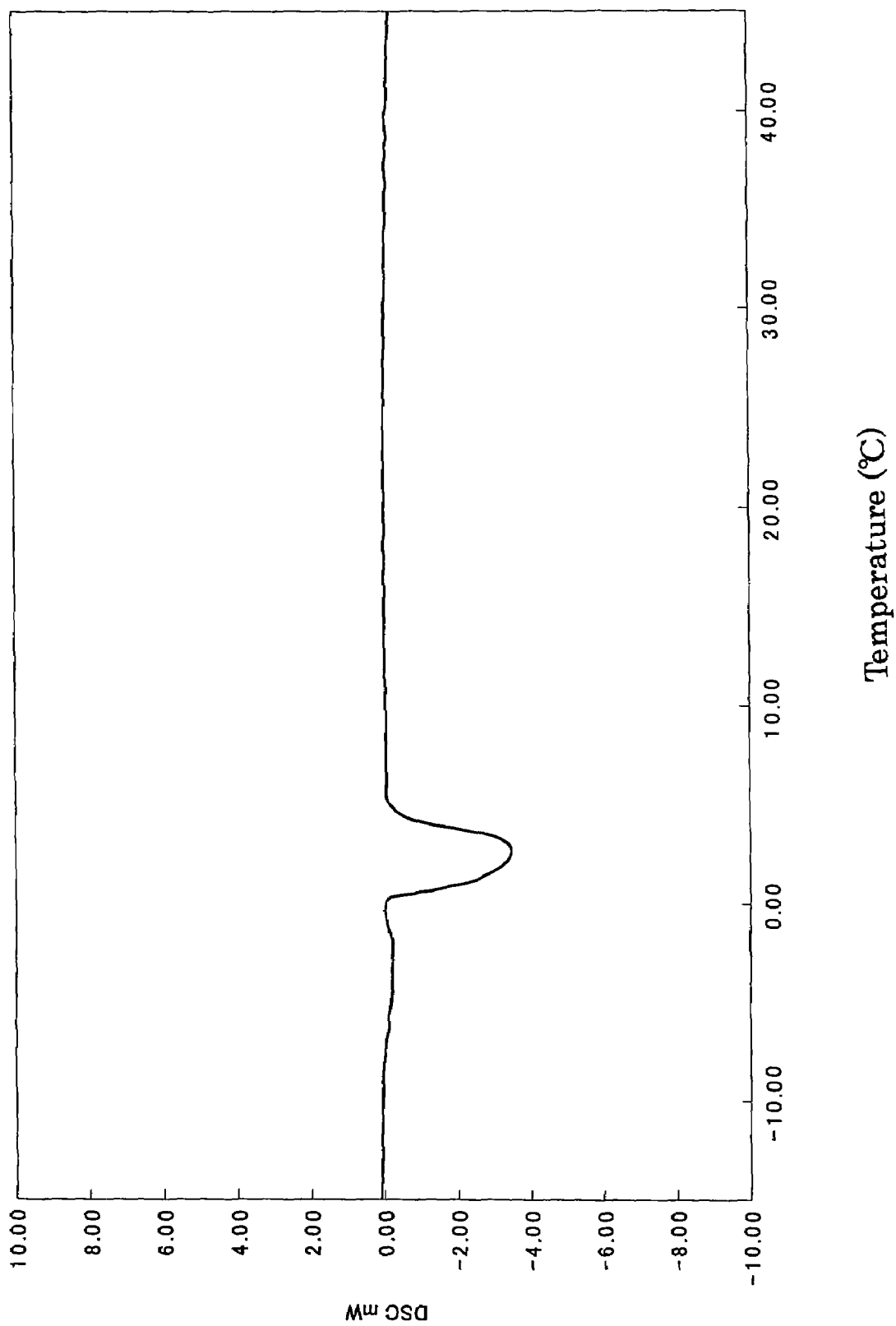
FIG. 5 is a graph showing the results of water-holding property test 2 of cholesteryl hydroxystearate.
Figure 6:
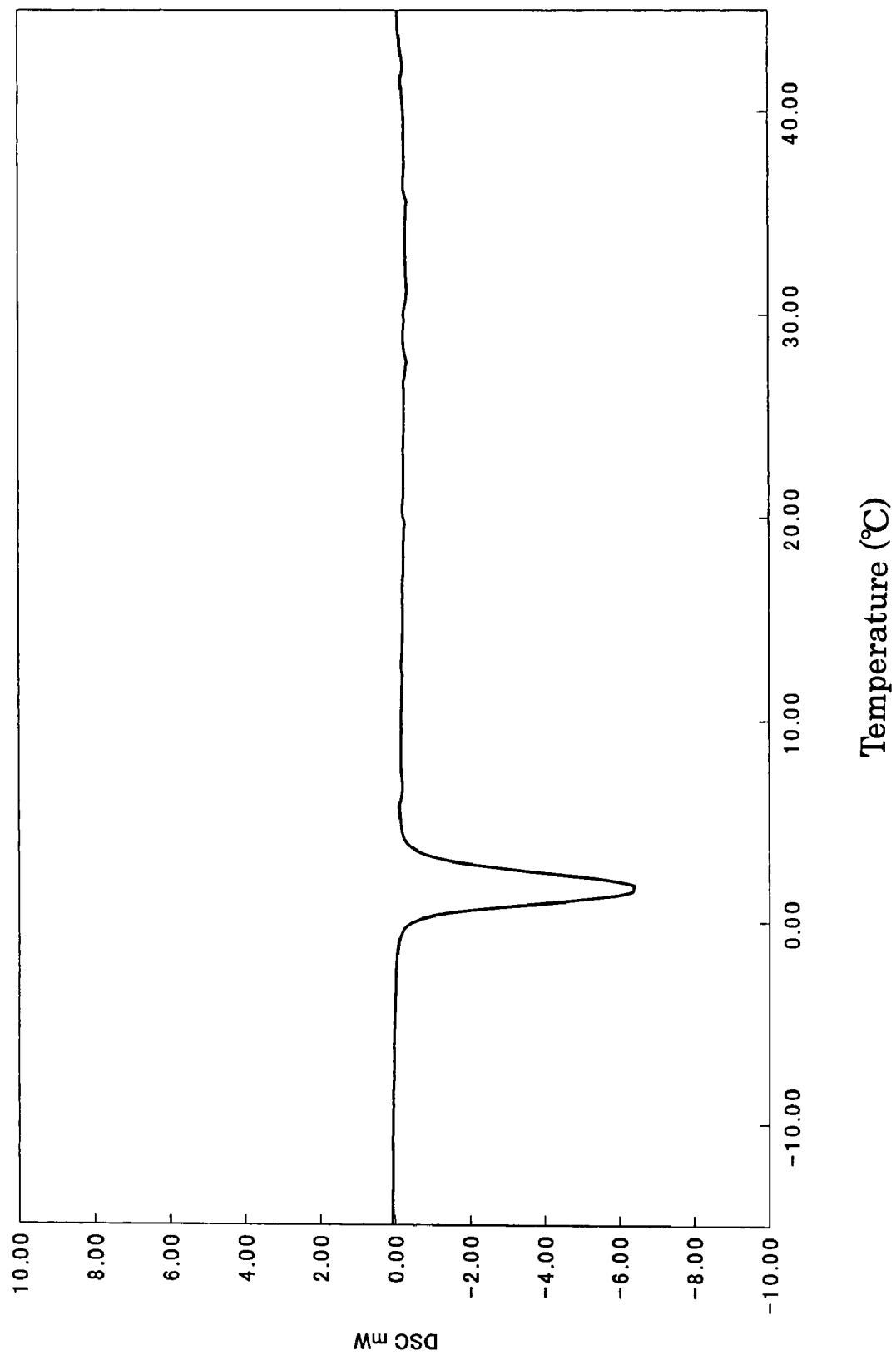
FIG. 6 is a graph showing the results of water-holding property test 2 of diisostearyl malate.
Figure 7:
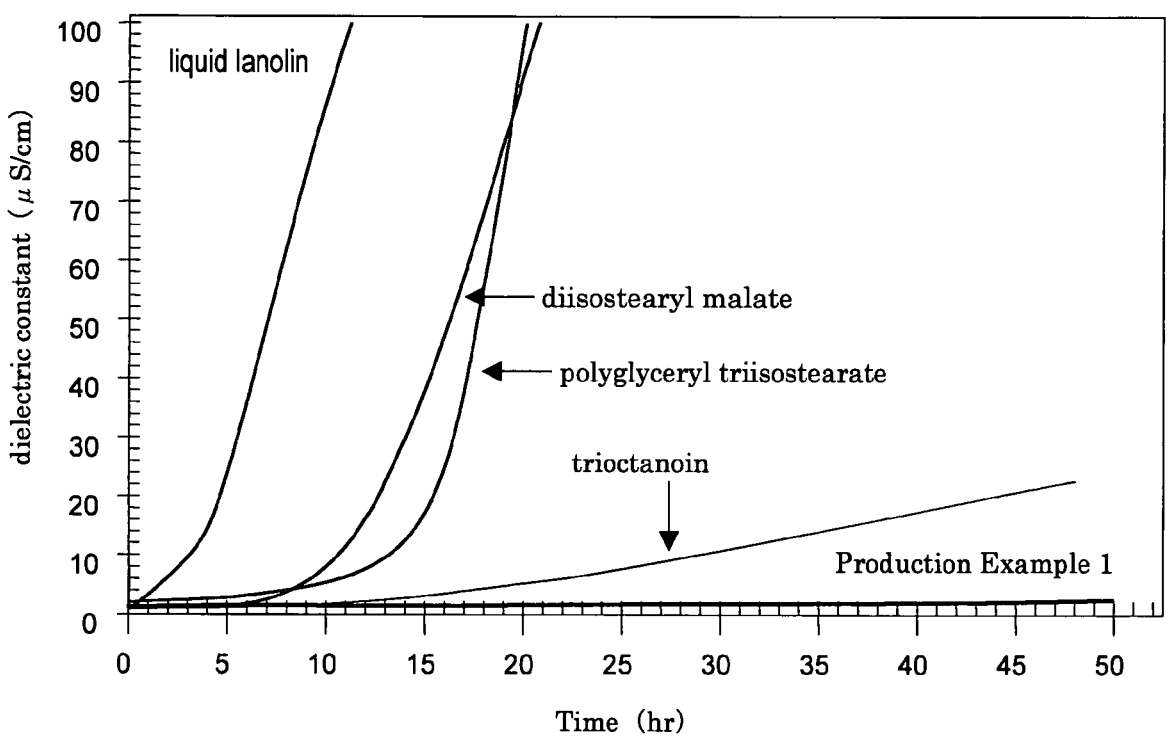
FIG. 7 is a graph showing the evaluation results of oxidative stability (CDM test).

FIGS. 4 to 6 are graphs showing the results of water-holding property test 2 of liquid lanolin, cholesteryl hydroxystearate, and diisostearyl malate, respectively. As shown in FIGS. 4 to 6, in each of these compounds, an endothermic peak due to water at around 0° C. was detected. This means that these compounds cannot hold a large amount of water as fine particles and are also not stable against temperature change.

TABLE 2

|  | Dyeing properties | Water resistant ability (difference in contact angle (°)) |
|---|---|---|
| Production Example 1 | ◯ | 4.3 |
| Production Example 2 | ◯ | 4.5 |
| Production Example 3 | Δ | 1.7 |
| Liquid lanolin | X | 32.5 |
| Polyglyceryl triisostearate | Δ | 21.0 |
| Diisostearyl malate | X | 47.4 |

The followings were confirmed by the results shown in Table 2. The esterification reaction products prepared in Production Examples 1 and 2 were excellent in the non-dyeing properties and had an effect to suppress the adhesion of dyes to skin. In addition, the difference in the contact angle between the film surface and the water droplet before and after washing was small in each of the esterification reaction products prepared in Production Examples 1 and 2, compared to those in liquid lanolin, polyglyceryl triisostearate, and diisostearyl malate. This means that these esterification reaction products are excellent in water resistance. In other words, the esterification reaction products prepared in Production Examples 1 and 2 are excellent in the non-dyeing properties and water resistance.

The evaluation results of oxidative stability are shown in FIG. 7. FIG. 7 is a graph showing the evaluation results of oxidative stability (CDM test). The horizontal axis represents elapsed time and the vertical axis represents dielectric constant. As shown in FIG. 7, the dielectric constant of the esterification reaction product prepared in Production Example 1 did not substantially vary with the lapse of time. Thus, it was confirmed that the esterification reaction product was very excellent in oxidative stability. In addition, the esterification reaction product did not have changes in the color tone and odor before and after the test, and thus it was confirmed that the esterification reaction product was also excellent in thermal stability. In other compounds used in this test, the dielectric constant increased with the lapse of time, and therefore it was confirmed that the oxidative stability of these compounds was inferior to that of the esterification reaction product prepared in Production Example 1. Furthermore, though it is not shown in the figure, the esterification reaction product prepared in Production Example 2 also had the same oxidative stability as that of the product in Production Example 1.

Then, cosmetic products were produced and were each evaluated. The evaluation of the cosmetic products was conducted by sensory evaluation as follows:

Sensory Evaluation of Cosmetic Product

Each cosmetic product was used by ten sensory evaluation panelists and evaluated for the following items: spread (whether or not the cosmetic product is smoothly spread on, for example, skin), moisturizing feeling (whether or not the cosmetic product moisturizes, for example, skin), gloss (whether or not the cosmetic product imparts natural gloss to, for example, hair), softness (whether or not the cosmetic product imparts softness to skin, hair, or the like), film-forming feeling (whether or not film-forming feeling is obtained after application of the cosmetic product), adhesion (whether or not adhesiveness is obtained after application of the cosmetic product), conditioning feeling (whether or not the cosmetic product imparts well-conditioning feeling to hair), dinginess (whether or not the cosmetic product is well clung to eyelashes), smoothness (whether or not the cosmetic product has smoothness upon application), curling feeling (whether or not the cosmetic product well curls eyelashes), tautness (whether or not the cosmetic product imparts tautness to the applied portion), shine (whether or not the cosmetic products imparts shine of the applied portion), effective length (whether or not the makeup lasts for a long time after application), color development (whether or not the cosmetic product develops bright color at the applied portion), impact resistance (whether or not the makeup is maintained against touching), cleansing properties (whether or not the cleansing ability is good), and hardness (whether or not the cosmetic product such as lip rouge has sufficient hardness). Each evaluation item was evaluated and was given an evaluation score according to the following evaluation criteria.

Evaluation Criteria

Score 6: very excellent

Score 5: excellent

Score 4: very good

Score 3: good

Score 2: bad

Score 1: poor

Score 0: very poor

In addition, the average scores of the 10 sensory evaluation panelists were calculated and the cosmetic products were evaluated based on the average scores according to the following evaluation criteria.

Score≧5: ◉(very excellent)
5>Score≧3: ○ (excellent)
3>Score≧1: Δ (borderline)
1>Score: X (particularly poor)

Example 1, Comparative Examples 1 and 2

Production of Stick-Type Lip Rouge

Stick-type lip rouge having the formula shown in Table 3 was produced by the following process. In the Examples shown below, the unit of numerals in Tables is "% by mass".

Raw materials 3 to 5 were added to a part of raw material 11, and the mixture was treated with a roller to prepare a pigment part. Raw material 6 was dissolved in a part of raw material 11 to prepare a dye part. Raw material or 2 was mixed with raw materials 7 to 15. The resulting mixture was melted by heating, and then the pigment part and the dye part were added thereto. The resulting mixture was uniformly dispersed with a homomixer. The resulting dispersion was poured into a mold and then rapidly cooled to obtain stick-type lip rouge. The lip rouge was sensorily evaluated. Table 4 shows the results.

TABLE 3

| Raw material | Example 1 | Comparative Example 1 | Comparative Example 2 |
|---|---|---|---|
| 1. Esterification reaction product (Production Example 2) | 11.0 | — | — |
| 2. Liquid lanolin | — | 11.0 | — |
| 3. Titanium dioxide | 5.0 | 5.0 | 5.0 |
| 4. Red No. 201 | 0.6 | 0.6 | 0.6 |
| 5. Red No. 202 | 1.0 | 1.0 | 1.0 |
| 6. Red No. 223 | 0.2 | 0.2 | 0.2 |
| 7. Candelilla wax | 9.0 | 9.0 | 9.0 |
| 8. Solid paraffin | 8.0 | 8.0 | 8.0 |
| 9. Beewax | 5.0 | 5.0 | 5.0 |
| 10. Carnauba wax | 5.0 | 5.0 | 5.0 |
| 11. Castor oil | 25.0 | 25.0 | 36.0 |
| 12. Cetyl 2-ethylhexanoate | 20.0 | 20.0 | 20.0 |
| 13. Isopropyl myristic acid ester | 10.0 | 10.0 | 10.0 |
| 14. Antioxidant | 0.1 | 0.1 | 0.1 |
| 15. Perfume | 0.1 | 0.1 | 0.1 |
| Total | 100.0 | 100.0 | 100.0 |

TABLE 4

| Sensory test | Example 1 | Comparative Example 1 | Comparative Example 2 |
|---|---|---|---|
| Spread | ◉ | ◉ | Δ |
| Moisturizing feeling | ◉ | ○ | ○ |
| Gloss | ◉ | ○ | Δ |

The followings were confirmed by the results shown in Table 4.

It was recognized that the stick-type lip rouge of Example 1 was smoothly spread on lips, imparted natural gloss to the lips, and had a moisturizing effect. In addition, the stick-type lip rouge of Example 1 had excellent effects compared to the stick-type lip rouge of Comparative Examples 1 and 2, and taste and odor were not felt. Furthermore, it was confirmed that the stick-type lip rouge of Example 1 reduced smudges.

Example 2 and Comparative Example 3

Production of Paste-Type Lip Rouge

Paste-type lip rouge having the formula shown in Table 5 was produced by the following process.

Raw materials 1 to 12 were uniformly mixed and melted by heating, and then raw materials 13 to 16 were added thereto. The resulting mixture was uniformly mixed and then put into a container to obtain paste-type lip rouge. The lip rouge was sensorily evaluated. Table 6 shows the results.

TABLE 5

| Raw material | Example 2 | Comparative Example 3 |
|---|---|---|
| 1. Esterification reaction product (Production Example 2) | 10.0 | — |
| 2. Lanolin | — | 10.0 |
| 3. 12-Hydroxystearic acid | 1.0 | 1.0 |
| 4. Dextrin fatty acid ester | 3.0 | 3.0 |
| 5. Dimethyldichlorosilane treated fumed silica | 1.0 | 1.0 |
| 6. Aluminum isostearate | 1.0 | 1.0 |
| 7. Heavy liquid isoparaffin | 25.0 | 25.0 |
| 8. Diglyceryl tetraisostearate | 20.0 | 20.0 |
| 9. Propylene glycol dicaprate | 10.0 | 10.0 |
| 10. Antioxidant | 0.1 | 0.1 |
| 11. 2-Hydroxy-4-methoxybenzophenone | 0.1 | 0.1 |
| 12. Diisostearyl malate | balance | balance |
| 13. Red No. 202 | 0.2 | 0.2 |
| 14. Yellow No. 4 | 1.2 | 1.2 |
| 15. Titanium oxide | 3.0 | 3.0 |
| 16. Black iron oxide | 0.2 | 0.2 |
| Total | 100.0 | 100.0 |

TABLE 6

| Sensory test | Example 2 | Comparative Example 3 |
|---|---|---|
| Effective length | ◉ | Δ |
| Color development | ◉ | ○ |
| Adhesion | ◉ | Δ |
| Film-forming feeling | ◉ | Δ |

The followings were confirmed by the results shown in Table 6.

It was recognized that the paste-type lip rouge of Example 2 was excellent in the color development of the pigment, adhesion, and film-forming feeling (uniformity of cosmetic film) and maintained makeup for a long time. In addition, the paste-type lip rouge of Example 2 was superior to the paste-type lip rouge of Comparative Example 3 in all the color development, adhesion, and film-forming feeling. The makeup also lasted for a longer time.

Example 3 and Comparative Example 4

Production of Stick-Type Lip Balm Containing Glycerin

Glycerin-containing stick-type lip balm having the formula shown in Table 7 was produced by the following process.

All raw materials were mixed and melted by heating, and then uniformly dispersed with a homomixer to obtain a dispersion. The resulting dispersion was poured into a mold and then rapidly cooled to obtain glycerin-containing stick-type lip balm.

The glycerin-containing material in Table 7 was prepared as follows:

The esterification reaction product prepared in Production Example 1 and Vaseline were mixed at a mass ratio of esterification reaction product:Vaseline=1:9 (mass ratio). This mixture was stirred while dropwise adding glycerin thereto up to an amount ten times the mixture to obtain a glycerin-containing material. The results of sensory evaluation are shown in Table 8.

TABLE 7

| Raw material | Example 3 | Comparative Example 4 |
| --- | --- | --- |
| 1. Glycerin-containing material | 1.1 | — |
| 2. Esterification reaction product (Production Example 1) | 5.0 | — |
| 3. Liquid lanolin | — | 5.0 |
| 4. Glycerin | — | 1.0 |
| 5. Ceresin | 6.0 | 6.0 |
| 6. Candelilla wax | 10.0 | 10.0 |
| 7. Microcrystalline wax | 4.0 | 4.0 |
| 8. Dipentaerythrityl (hydroxystearate/stearate/rosinate) | 10.0 | 10.0 |
| 9. Castor oil | 17.0 | 17.0 |
| 10. Trioctanoin | 15.0 | 15.0 |
| 11. Polyglyceryl triisostearate | balance | balance |
| Total | 100.0 | 100.0 |

TABLE 8

| Sensory test | Example 3 | Comparative Example 4 |
| --- | --- | --- |
| Moisturizing feeling | ◎ | Δ |
| Spread | ◎ | Δ |
| Gloss | ◎ | ○ |

The followings were confirmed by the results shown in Table 8.

It was recognized that the glycerin-containing stick-type lip balm of Example 3 was excellent in the moisturizing feeling, smoothly spread on lips, and imparted natural gloss to the lips. In addition, the glycerin-containing stick-type lip balm of Example 3 was superior to the stick-type lip balm of Comparative Example 4 in all the moisturizing feeling, spread, and gloss. Furthermore, taste and odor were not felt.

Example 4 and Comparative Example 5

Production of Stick-Type Lip Rouge Containing Vitamin C Derivative

Vitamin C derivative-containing stick-type lip rouge having the formula shown in Table 9 was produced by the following process.

All raw materials were mixed and melted by heating, and then uniformly dispersed with a homomixer to obtain a dispersion. The resulting dispersion was poured into a mold and then rapidly cooled to obtain vitamin C derivative-containing stick-type lip rouge.

The vitamin C derivative-containing material in Table 9 was prepared as follows:

The esterification reaction product prepared in Production Example 1 and Vaseline were mixed at a mass ratio of esterification reaction product:Vaseline=1:9 (mass ratio). This mixture was stirred while dropwise adding a 20% magnesium-L-ascorbyl-phosphate aqueous solution thereto up to an amount ten times the mixture to obtain a vitamin C derivative-containing material. The results of sensory evaluation are shown in Table 10.

TABLE 9

| Raw material | Example 4 | Comparative Example 5 |
| --- | --- | --- |
| 1. Vitamin C derivative-containing material | 1.1 | — |
| 2. Esterification reaction product (Production Example 1) | 5.0 | — |
| 3. Liquid lanolin | — | 5.0 |
| 4. Vitamin C derivative aqueous solution | — | 1.0 |
| 5. Celesin | 8.0 | 8.0 |
| 6. Candelilla wax | 10.0 | 10.0 |
| 7. Microcrystalline wax | 4.0 | 4.0 |
| 8. Dipentaerythrityl (hydroxystearate/stearate/rosinate) | 10.0 | 10.0 |
| 9. Diisostearyl malate | 17.0 | 17.0 |
| 10. Trioctanoin | 10.0 | 10.0 |
| 11. Polyglyceryl triisostearate | balance | balance |
| Total | 100.0 | 100.0 |

TABLE 10

| Sensory test | Example 4 | Comparative Example 5 |
| --- | --- | --- |
| Moisturizing feeling | ◎ | X |
| Spread | ◎ | X |
| Gloss | ◎ | X |
| Hardness | ◎ | X |

The followings were confirmed by the results shown in Table 10.

It was recognized that the vitamin C derivative-containing stick-type lip rouge of Example 4 was excellent in the moisturizing feeling, smoothly spread on lips, imparted natural gloss to the lips, and also had sufficient hardness. In addition, these effects of the vitamin C derivative-containing stick-type lip rouge of Example 4 were higher than those of the stick-type lip rouge of Comparative Example 5. Furthermore, taste and odor were not felt.

Example 5 and Comparative Example 6

Production of Liquid Foundation (O/W Type)

Liquid foundation (O/W type) having the formula shown in Table 11 was produced by the following process.

Raw material 18 was dispersed in raw material 10, and then raw materials 19 and 20 were added thereto. The resulting mixture was treated with a homomixer at 70° C., and then the remaining aqueous ingredients (raw materials 11 and 12) were added thereto. The resulting mixture was thoroughly mixed to prepare an aqueous phase. Then, powder ingredients (raw materials 13 to 17) were sufficiently mixed and pulverized and then added to the aqueous phase while stirring. The mixture was treated with a homomixer at 70° C.

At the same time, raw material 1 or 2 and oil ingredients (raw materials 3 to 8) were dissolved by heating at 70 to 80° C. to prepare an oil phase. Then, this oil phase was gradually added to the aqueous phase containing the powder ingredients. The resulting mixture was treated with a homomixer at 70° C. and then cooled to 45° C. while stirring, and then raw material 9 was added thereto. After cooling to room temperature, the cooled mixture was deaerated and put in a container to obtain liquid foundation (O/W type). The results of sensory evaluation are shown in Table 12.

TABLE 11

| Raw material | Example 5 | Comparative Example 6 |
|---|---|---|
| 1. Esterification reaction product (Production Example 1) | 1.5 | — |
| 2. Cholesteryl hydroxystearate | — | 1.5 |
| 3. Squalane | 3.0 | 3.0 |
| 4. Liquid paraffin | 3.0 | 3.0 |
| 5. Dimethyl polysiloxane | 0.2 | 0.2 |
| 6. Stearic acid | 2.5 | 2.5 |
| 7. Sorbitan sesquioleate | 1.0 | 1.0 |
| 8. Cetyl alcohol | 0.5 | 0.5 |
| 9. 1% Sodium hydroxide aqueous solution | 1.3 | 1.3 |
| 10. 1% Carboxyvinyl polymer aqueous solution | 5.0 | 5.0 |
| 11. 1,3-Butylene glycol | 8.0 | 8.0 |
| 12. Triethanolamine | 0.7 | 0.7 |
| 13. Talc | 3.0 | 3.0 |
| 14 Titanium dioxide | 5.0 | 5.0 |
| 15. Bengara | 0.5 | 0.5 |
| 16. Yellow iron oxide | 1.4 | 1.4 |
| 17. Black iron oxide | 0.1 | 0.1 |
| 18. Bentonite | 0.5 | 0.5 |
| 19. Preservative | 0.1 | 0.1 |
| 20. Purified water | 62.7 | 62.7 |
| Total | 100.0 | 100.0 |

TABLE 12

| Sensory test | Example 5 | Comparative Example 6 |
|---|---|---|
| Film-forming feeling | ◎ | Δ |
| Adhesion | ◎ | ○ |
| Moisturizing feeling | ◎ | ◎ |
| Softness | ○ | ○ |

The followings were confirmed by the results shown in Table 12.

It was recognized that the liquid foundation (O/W type) of Example 5 well adhered to skin and moisturized and softened the skin. It was confirmed that the liquid foundation (O/W type) of Example 5 was superior to the liquid foundation (O/W type) of Comparative Example 6 in all the film-forming feeling, adhesion, moisturizing feeling, and softness.

Example 6 and Comparative Example 7

Production of Foundation (W/O Type)

Foundation (W/O type) having the formula shown in Table 13 was produced by the following process.

Raw materials 1 to 9 were mixed and melted by heating and then cooled to 40° C., and then raw materials 10 to 18 were added to thereto. The resulting mixture was dispersed with a homomixer to obtain mixture (A). At the same time, raw materials 19 to 24 were uniformly mixed and dissolved to obtain mixture (B). Then, mixture (B) was added to mixture (A), and the resulting mixture was emulsified with a homomixer to obtain foundation (W/O type). The results of sensory evaluation are shown in Table 14.

TABLE 13

| Raw material | Example 6 | Comparative Example 7 |
|---|---|---|
| 1. Esterification reaction product (Production Example 1) | 10.0 | — |
| 2. Diisostearyl malate | — | 10.0 |

TABLE 13-continued

| Raw material | Example 6 | Comparative Example 7 |
|---|---|---|
| 3. Trioctanoin | 20.0 | 20.0 |
| 4. Dimethyl polysiloxane (20 cs) | 1.0 | 1.0 |
| 5. Octamethylcyclotetrasiloxane | 5.0 | 5.0 |
| 6. Squalane | 5.0 | 5.0 |
| 7. Cetyl 2-ethylhexanoate | 2.0 | 2.0 |
| 8. Polyether-modified polysiloxane | 3.0 | 3.0 |
| 9. Sorbitan sesquioleate | 1.0 | 1.0 |
| 10. Titanium oxide | 7.0 | 7.0 |
| 11. Zinc oxide | 4.0 | 4.0 |
| 12. Talc | 4.7 | 4.7 |
| 13. Mica | 2.0 | 2.0 |
| 14. Red iron oxide | 0.2 | 0.2 |
| 15. Yellow iron oxide | 1.6 | 1.6 |
| 16. Black iron oxide | 0.2 | 0.2 |
| 17. Nylon powder | 2.0 | 2.0 |
| 18. Titanated mica | 2.0 | 2.0 |
| 19. Ethyl alcohol | 5.0 | 5.0 |
| 20. Glycerin | 5.0 | 5.0 |
| 21. Antioxidant | 0.1 | 0.1 |
| 22. Moisturizing agent | 0.1 | 0.1 |
| 23. Perfume | 0.1 | 0.1 |
| 24. Purified water | balance | balance |
| Total | 100.0 | 100.0 |

TABLE 14

| Sensory test | Example 6 | Comparative Example 7 |
|---|---|---|
| Effective length | ◎ | Δ |
| Adhesion | ○ | Δ |
| Spread | ◎ | ○ |
| Film-forming feeling | ◎ | Δ |

The followings were confirmed by the results shown in Table 14.

It was recognized that the foundation (W/O type) of Example 6 was excellent in adhesion to skin, spread, and film-forming feeling (uniformity of cosmetic film), and the makeup was maintained for a long time. In addition, it was confirmed that the foundation (W/O type) of Example 6 was superior to the foundation (W/O type) of Comparative Example 7 in all the adhesion, spread, and film-forming feeling. Furthermore, the makeup was maintained for a longer time.

Example 7 and Comparative Example 8

Production of Solid Powder Foundation

Solid powder foundation having the formula shown in Table 15 was produced by the following process.

Raw materials 1 to 4 were mixed and heated to 50° C. to obtain mixture (A). At the same time, raw materials 5 to 13 were mixed and dispersed and were then mixed with mixture (A) to obtain mixture (B). The resulting mixture (B) was pulverized and compression molded into a plate to obtain solid powder foundation. The results of sensory evaluation are shown in Table 16.

TABLE 15

| Raw material | Example 7 | Comparative Example 8 |
|---|---|---|
| 1. Esterification reaction product (Production Example 1) | 10.0 | — |
| 2. Liquid lanolin | — | 10.0 |

TABLE 15-continued

| Raw material | Example 7 | Comparative Example 8 |
|---|---|---|
| 3. Dimethyl polysiloxane | 2.0 | 2.0 |
| 4. Squalane | 5.0 | 5.0 |
| 5. Polystyrene | 2.0 | 2.0 |
| 6. Titanium oxide | 5.0 | 5.0 |
| 7. Bengara | 0.5 | 0.5 |
| 8. Yellow iron oxide | 1.2 | 1.2 |
| 9. Black iron oxide | 0.1 | 0.1 |
| 10. Sericite | 50.0 | 50.0 |
| 11. Mica | 20.0 | 20.0 |
| 12. Talc | 3.7 | 3.7 |
| 13. Preservative | 0.5 | 0.5 |
| Total | 100.0 | 100.0 |

TABLE 16

| Sensory test | Example 7 | Comparative Example 8 |
|---|---|---|
| Effective length | ◉ | Δ |
| Adhesion | ◉ | ○ |
| Film-forming feeling | ◉ | Δ |

The followings were confirmed by the results shown in Table 16.

It was recognized that the solid powder foundation of Example 7 was excellent in adhesion to skin, film-forming feeling (uniformity of cosmetic film), and the makeup was maintained for a long time. In addition, it was confirmed that the solid powder foundation of Example 7 was superior to the solid powder foundation of Comparative Example 8 in both the adhesion and film-forming feeling. Furthermore, the makeup was maintained for a longer time.

Example 8 and Comparative Example 9

Production of Solid Face Powder

Solid face powder having the formula shown in Table 17 was produced by the following process.

Raw materials 6 to 10 were mixed and dispersed to obtain mixture (A). Raw materials 1 to 5 were added to mixture (A), and the resulting mixture was uniformly mixed to obtain mixture (B). The resulting mixture (B) was pulverized and compression molded into a plate to obtain solid face powder. The results of sensory evaluation are shown in Table 18.

TABLE 17

| Raw material | Example 8 | Comparative Example 9 |
|---|---|---|
| 1. Esterification reaction product (Production Example 2) | 10.0 | — |
| 2. Esterification reaction product (Production Example 3) | — | 10.0 |
| 3. Dimethyl polysiloxane | 1.0 | 1.0 |
| 4. Liquid paraffin | 5.0 | 5.0 |
| 5. Dipentaerythrite fatty acid ester | 0.5 | 0.5 |
| 6. Preservative | 0.5 | 0.5 |
| 7. Iron oxide titanated mica | 20.0 | 20.0 |
| 8. Sericite | 55.5 | 55.5 |
| 9. Red No. 202 | 0.5 | 0.5 |
| 10. Spherical silica | 7.0 | 7.0 |
| Total | 100.0 | 100.0 |

TABLE 18

| Sensory test | Example 8 | Comparative Example 9 |
|---|---|---|
| Effective length | ◉ | ○ |
| Adhesion | ◉ | ○ |
| Film-forming feeling | ◉ | Δ |

The followings were confirmed by the results shown in Table 18.

It was recognized that the solid face powder of Example 8 was excellent in adhesion to skin, film-forming feeling (uniformity of cosmetic film), and the makeup was maintained for a long time. In addition, it was confirmed that the solid face powder of Example 8 was superior to the solid face powder of Comparative Example 9 in both the adhesion and film-forming feeling. Furthermore, the makeup was maintained for a longer time.

Example 9 and Comparative Example 10

Production of Powder Cake Foundation (Using Water)

Powder cake foundation having the formula shown in Table 19 was produced by the following process.

Raw materials 8 to 15 were mixed and dispersed to obtain mixture (A). At the same time, raw materials 1 to 6 were mixed under heating to 50° C. to obtain mixture (B). Then, mixture (B) and raw material 7 were added to mixture (A), and the resulting mixture was uniformly mixed to obtain mixture (C). Then, the resulting mixture (C) was pulverized and compression molded into a plate to obtain powder cake foundation. The results of sensory evaluation are shown in Table 20.

TABLE 19

| Raw material | Example 9 | Comparative Example 10 |
|---|---|---|
| 1. Esterification reaction product (Production Example 1) | 5.0 | — |
| 2. Diisostearyl malate | — | 5.0 |
| 3. POE-sorbitan monooleate (20 E.O.) | 1.0 | 1.0 |
| 4. Trioctanoin | 4.0 | 4.0 |
| 5. Dimethyl polysiloxane | 5.0 | 5.0 |
| 6. Dipropylene glycol | 3.0 | 3.0 |
| 7. Perfume | 0.1 | 0.1 |
| 8. Silicone-treated talc*1 | 50.0 | 50.0 |
| 9. Fluorine-treated sericite*2 | 17.1 | 17.1 |
| 10. Titanated mica | 2.0 | 2.0 |
| 11. Bengara | 0.5 | 0.5 |
| 12. Yellow iron oxide | 2.0 | 2.0 |
| 13. Black iron oxide | 0.3 | 0.3 |
| 14. Boron nitride powder | 5.0 | 5.0 |
| 15. Nylon powder | 5.0 | 5.0 |
| Total | 100.0 | 100.0 |

TABLE 20

| Sensory test | Example 9 | Comparative Example 10 |
|---|---|---|
| Effective length | ◉ | Δ |
| Adhesion | ○ | Δ |
| Spread | ◉ | Δ |

In Table 19, the raw material indicated by *1 was treated with 5% by weight of methyl hydrogen polysiloxane, and the raw material indicated by *2 was treated with 5% by weight of a perfluoroalkyl phosphate ester diethanolamine salt.

The followings were confirmed by the results shown in Table 20.

It was recognized that the powder cake foundation of Example 9 well adhered and spread on skin, and the makeup was maintained for a long time. In addition, these effects of the powder cake foundation of Example 9 were higher than those of the powder cake foundation of Comparative Example 10. Furthermore, the makeup was maintained for a longer time.

Example 10 and Comparative Example 11

Production of Powder Eye Color

Powder eye color having the formula shown in Table 21 was produced by the following process.

Raw materials 3 to 8 were uniformly mixed and dispersed to obtain mixture (A), and raw materials 1 and 2 were added to mixture (A). The resulting mixture was pulverized to obtain powder eye color. The results of sensory evaluation are shown in Table 22.

TABLE 21

| Raw material | Example 10 | Comparative Example 11 |
|---|---|---|
| 1. Esterification reaction product (Production Example 1) | 10.0 | — |
| 2. Diisostearyl malate | — | 10.0 |
| 3. Sericite | 12.9 | 12.9 |
| 4. Mica | 30.0 | 30.0 |
| 5. Red No. 202 | 2.0 | 2.0 |
| 6. Titanated mica | 40.0 | 40.0 |
| 7. Nylon powder | 5.0 | 5.0 |
| 8. Preservative | 0.1 | 0.1 |
| Total | 100.0 | 100.0 |

TABLE 22

| Sensory test | Example 10 | Comparative Example 11 |
|---|---|---|
| Effective length | ⊚ | Δ |
| Adhesion | ⊚ | ○ |
| Spread | ○ | Δ |

The followings were confirmed by the results shown in Table 22.

It was recognized that the powder eye color of Example well adhered and spread on skin, and the makeup was maintained for a long time. In addition, these effects of the powder eye color of Example 10 were higher than those of the powder eye color of Comparative Example 11. Furthermore, the makeup was maintained for a longer time.

Example 11 and Comparative Example 12

Production of Eye Color

Eye color having the formula shown in Table 23 was produced by the following process.

Raw materials 1 to 6 were mixed and dissolved to obtain mixture (A). Raw materials 13 to 18 were heated to 80° C., and raw materials 7 to 12 were added thereto. The resulting mixture was dispersed with a homomixer to obtain a dispersion (B). Then, dispersion (B) was added to mixture (A), and the resulting mixture was treated with a homomixer and then cooled to obtain eye color. The results of sensory evaluation are shown in Table 24.

TABLE 23

| Raw material | Example 11 | Comparative Example 12 |
|---|---|---|
| 1. Esterification reaction product (Production Example 1) | 7.0 | — |
| 2. Diisostearyl malate | — | 7.0 |
| 3. Sorbitan tristearate | 0.05 | 0.05 |
| 4. POE-Sorbitan trioleate (20 E.O.) | 0.1 | 0.1 |
| 5. Stearic acid | 0.4 | 0.4 |
| 6. Isostearic acid | 0.5 | 0.5 |
| 7. Red No. 226 | 1.0 | 1.0 |
| 8. Silicone-treated bengara* | 1.0 | 1.0 |
| 9. Silicone-treated titanium oxide* | 0.5 | 0.5 |
| 10. Silicone-treated titanated mica* | 5.0 | 5.0 |
| 11. Silicone-treated talc* | 3.0 | 3.0 |
| 12. Methyl polymethacrylate spherical powder | 2.0 | 2.0 |
| 13. Ethyl alcohol | 5.0 | 5.0 |
| 14. Triethanolamine | 0.8 | 0.8 |
| 15. Glycerin | 3.0 | 3.0 |
| 16. Polyethylene glycol (400) | 3.0 | 3.0 |
| 17. Preservative | 0.1 | 0.1 |
| 18. Purified water | balance | balance |
| Total | 100.0 | 100.0 |

In Table 23, the raw material indicated by * was treated with 5% by weight of dimethyl polysiloxane.

TABLE 24

| Sensory test | Example 11 | Comparative Example 12 |
|---|---|---|
| Effective length | ⊚ | Δ |
| Adhesion | ⊚ | Δ |
| Film-forming feeling | ⊚ | Δ |

The followings were confirmed by the results shown in Table 24.

It was recognized that the eye color of Example 11 was excellent in adhesion and film-forming feeling (uniformity of cosmetic film), and the makeup was maintained for a long time. In addition, the eye color of Example 11 was superior to the eye color of Comparative Example 12 in both the adhesion and film-forming feeling. Furthermore, the makeup was maintained for a longer time.

Example 12 and Comparative Example 13

Production of Mascara (O/W Type)

Mascara (O/W type) having the formula shown in Table 25 was produced by the following process.

Raw materials 1 to 9 were dissolved by heating, and raw materials 10 to 12 were added thereto. The resulting mixture was uniformly mixed to obtain mixture (A). At the same time, raw materials 13 to 21 were uniformly mixed to obtain mixture (B). Then, mixture (B) was added to mixture (A), and the resulting mixture was emulsified to obtain mascara (O/W type). The results of sensory evaluation are shown in Table 26.

TABLE 25

| Raw material | Example 12 | Comparative Example 13 |
|---|---|---|
| 1. Esterification reaction product (Production Example 1) | 3.0 | — |
| 2. Lanolin | — | 3.0 |
| 3. Stearic acid | 2.0 | 2.0 |
| 4. Carnauba wax | 4.0 | 4.0 |
| 5. Beeswax | 6.0 | 6.0 |

TABLE 25-continued

| Raw material | Example 12 | Comparative Example 13 |
| --- | --- | --- |
| 6. Cetyl alcohol | 1.0 | 1.0 |
| 7. Glyceryl monostearate | 1.0 | 1.0 |
| 8. POE-sorbitan monooleate (20 E.O.) | 1.5 | 1.5 |
| 9. Sorbitan sesquioleate | 0.5 | 0.5 |
| 10. Blue No. 1 | 1.0 | 1.0 |
| 11. Yellow No. 4 | 1.0 | 1.0 |
| 12. Iron oxide-coated titanated mica | 5.0 | 5.0 |
| 13. Silica | 2.5 | 2.5 |
| 14. Triethanolamine | 1.1 | 1.1 |
| 15. 1,3-Butylene glycol | 10.0 | 10.0 |
| 16. Polyvinyl acetate emulsion | 15.0 | 15.0 |
| 17. Nylon fiber | 4.0 | 4.0 |
| 18. Carboxyvinyl polymer | 0.2 | 0.2 |
| 19. Preservative | 0.1 | 0.1 |
| 20. Beauty ingredient | 0.1 | 0.1 |
| 21. Purified water | balance | balance |
| Total | 100.0 | 100.0 |

TABLE 26

| Sensory test | Example 12 | Comparative Example 13 |
| --- | --- | --- |
| Effective length | ◉ | Δ |
| Adhesion | ◉ | Δ |
| Film-forming feeling | ◉ | ○ |
| Impact resistance | ◉ | Δ |

The followings were confirmed by the results shown in Table 26.

It was recognized that the mascara (O/W type) of Example 12 was excellent in adhesion to skin, film-forming feeling (uniformity of cosmetic film), and impact resistance, and the makeup was maintained for a long time. In addition, the mascara (O/W type) of Example 12 was superior to the mascara (O/W type) of Comparative Example 13 in all the adhesion, film-forming feeling, and impact resistance. Furthermore, the makeup was maintained for a longer time.

Example 13 and Comparative Example 14

Production of Mascara

Mascara having the formula shown in Table 27 was produced by the following process.

Raw material 6 was added to raw material 9. The resulting mixture was dispersed with a homomixer, and raw material 5 was added thereto. The resulting mixture was heated to and maintained at 70° C. (phase A). Other raw materials were mixed and heated to 70° C. (phase B). Phase A was added to phase B, and the mixture was uniformly dispersed and emulsified to obtain mascara. The results of sensory evaluation are shown in Table 28.

TABLE 27

| Raw material | Example 13 | Comparative Example 14 |
| --- | --- | --- |
| 1. Esterification reaction product (Production Example 2) | 8.0 | — |
| 2. Lanolin | — | 8.0 |
| 3. Paraffin wax | 8.0 | 8.0 |
| 4. Light isoparaffin | 30.0 | 30.0 |
| 5. Alkyl acrylate copolymer emulsion | 30.0 | 30.0 |
| 6. Iron oxide | 10.0 | 10.0 |
| 7. Sorbitan sesquioleate | 4.0 | 4.0 |

TABLE 27-continued

| Raw material | Example 13 | Comparative Example 14 |
| --- | --- | --- |
| 8. Preservative | 0.1 | 0.1 |
| 9. Purified water | balance | balance |
| Total | 100.0 | 100.0 |

TABLE 28

| Sensory test | Example 13 | Comparative Example 14 |
| --- | --- | --- |
| Clinginess | ◉ | Δ |
| Smoothness | ◉ | ○ |
| Curling feeling | ◉ | ○ |
| Tautness | ◉ | Δ |

The followings were confirmed by the results shown in Table 28.

It was recognized that the mascara of Example 13 readily clung to eyelashes and was smooth, and tautness and curling feeling were obtained. In addition, these effects of the mascara of Example 13 were higher than those of the mascara in Comparative Example 14. Furthermore, no odor was felt.

Example 14 and Comparative Example 15

Production of Eyeliner (O/W Type)

Eyeliner (O/W type) having the formula shown in Table 29 was produced by the following process.

Raw materials 1 to 5 were dissolved by heating, and raw materials 6 and 7 were added thereto. The resulting mixture was uniformly mixed to obtain mixture (A). At the same time, raw materials 8 to 14 were uniformly mixed to obtain mixture (B). Then, mixture (B) was added to mixture (A), and the resulting mixture was emulsified to obtain eyeliner (O/W type). The results of sensory evaluation are shown in Table 30.

TABLE 29

| Raw material | Example 14 | Comparative Example 15 |
| --- | --- | --- |
| 1. Esterification reaction product (Production Example 1) | 0.5 | — |
| 2. Diisostearyl malate | — | 0.5 |
| 3. Stearic acid | 1.0 | 1.0 |
| 4. Cetyl alcohol | 1.0 | 1.0 |
| 5. Glyceryl monostearate | 0.5 | 0.5 |
| 6. Ultramarine blue | 1.0 | 1.0 |
| 7. Red No. 202 | 1.0 | 1.0 |
| 8. 1,3-Butylene glycol | 5.0 | 5.0 |
| 9. Sodium hydroxide | 0.2 | 0.2 |
| 10. Alkyl acrylate copolymer emulsion | 10.0 | 10.0 |
| 11. Titanated mica | 10.0 | 10.0 |
| 12. Perfume | 0.1 | 0.1 |
| 13. Preservative | 0.1 | 0.1 |
| 14. Purified water | balance | balance |
| Total | 100.0 | 100.0 |

TABLE 30

| Sensory test | Example 14 | Comparative Example 15 |
| --- | --- | --- |
| Effective length | ◉ | ○ |
| Film-forming feeling | ◉ | Δ |
| Color development | ◉ | Δ |

The followings were confirmed by the results shown in Table 30.

It was recognized that the eyeliner (O/W type) of Example 14 was excellent in film-forming feeling (uniformity of cosmetic film) and color development, and the makeup was maintained for a long time. In addition, the eyeliner (O/W type) of Example 14 was superior to the eyeliner (O/W type) of Comparative Example 15 in both the film-forming feeling and color development. Furthermore, the makeup was maintained for a longer time.

Example 15 and Comparative Example 16

Production of Eyeshadow (O/W Type)

Eyeshadow (O/W type) having the formula shown in Table 31 was produced by the following process.

Raw materials 1 to 7 were dissolved by heating, and raw materials 8 and 9 were added thereto. The resulting mixture was uniformly mixed to obtain mixture (A). At the same time, raw materials 10 to 15 were uniformly mixed to obtain mixture (B). Then, mixture (B) was added to mixture (A), and the resulting mixture was emulsified to obtain eyeshadow (O/W type). The results of sensory evaluation are shown in Table 32.

TABLE 31

| Raw material | Example 15 | Comparative Example 16 |
|---|---|---|
| 1. Esterification reaction product (Production Example 2) | 40.0 | — |
| 2. Diisostearyl malate | — | 40.0 |
| 3. Stearic acid | 1.5 | 1.5 |
| 4. Cetyl alcohol | 1.0 | 1.0 |
| 5. POE-sorbitan monooleate (20 E.O.) | 0.5 | 0.5 |
| 6. Glyceryl monostearate | 0.5 | 0.5 |
| 7. Sorbitan sesquioleate | 0.5 | 0.5 |
| 8. Yellow No. 205 | 1.0 | 1.0 |
| 9. Red No. 226 | 1.0 | 1.0 |
| 10. Dipropylene glycol | 5.0 | 5.0 |
| 11. Carboxyvinyl polymer | 0.1 | 0.1 |
| 12. Triethanolamine | 0.8 | 0.8 |
| 13. Titanium oxide-treated synthetic phlogopite | 10.0 | 10.0 |
| 14. Preservative | 0.1 | 0.1 |
| 15. Purified water | balance | balance |
| Total | 100.0 | 100.0 |

TABLE 32

| Sensory test | Example 15 | Comparative Example 16 |
|---|---|---|
| Effective length | ◎ | Δ |
| Film-forming feeling | ◎ | ○ |
| Color development | ◎ | ○ |

The followings were confirmed by the results shown in Table 32.

It was recognized that the eyeshadow (O/W type) of Example 15 was excellent in film-forming feeling (uniformity of cosmetic film) and color development, and the makeup was maintained for a long time. In addition, the eyeshadow (O/W type) of Example 15 was superior to the eyeshadow (O/W type) of Comparative Example 16 in both the film-forming feeling and color development. Furthermore, the makeup was maintained for a longer time.

Example 16 and Comparative Example 17

Production of Eyebrow (O/W Type)

Eyebrow (O/W type) having the formula shown in Table 33 was produced by the following process.

Raw materials 1 to 7 were dissolved by heating, and raw material 8 was added thereto. The resulting mixture was uniformly mixed to obtain mixture (A). At the same time, raw materials 9 to 13 were uniformly mixed to obtain mixture (B). Then, mixture (B) was added to mixture (A), and the resulting mixture was emulsified to obtain eyebrow (O/W type). The results of sensory evaluation are shown in Table 34.

TABLE 33

| Raw material | Example 16 | Comparative Example 17 |
|---|---|---|
| 1. Esterification reaction product (Production Example 1) | 10.0 | — |
| 2. Diisostearyl malate | — | 10.0 |
| 3. Stearic acid | 3.0 | 3.0 |
| 4. Cetyl alcohol | 2.0 | 2.0 |
| 5. Ethylene glycol monostearate | 0.5 | 0.5 |
| 6. Glyceryl monostearate | 0.5 | 0.5 |
| 7. Sucrose fatty acid ester | 1.5 | 1.5 |
| 8. Black iron oxide | 1.0 | 1.0 |
| 9. 1,3-Butylene glycol | 5.0 | 5.0 |
| 10. Sodium hydroxide | 0.2 | 0.2 |
| 11. Preservative | 0.1 | 0.1 |
| 12. Alkyl acrylate copolymer emulsion | 10.0 | 10.0 |
| 13. Purified water | balance | balance |
| Total | 100.0 | 100.0 |

TABLE 34

| Sensory test | Example 16 | Comparative Example 17 |
|---|---|---|
| Effective length | ◎ | Δ |
| Film-forming feeling | ◎ | Δ |
| Color development | ◎ | ○ |

The followings were confirmed by the results shown in Table 34.

It was recognized that the eyebrow (O/W type) of Example 16 was excellent in film-forming feeling (uniformity of cosmetic film) and color development, and the makeup was maintained for a long time. In addition, the eyebrow (O/W type) of Example 16 was superior to the eyebrow (O/W type) of Comparative Example 17 in both the film-forming feeling and color development. Furthermore, the makeup was maintained for a longer time.

Example 17 and Comparative Example 18

Production of Eyegloss (Paste Type)

Eyegloss (paste type) having the formula shown in Table was produced by the following process.

Raw materials 1 to 10 were uniformly mixed and dissolved by heating to obtain a mixture. Then, the mixture was put into a container to obtain eyegloss (paste type). The results of sensory evaluation are shown in Table 36.

TABLE 35

| Raw material | Example 17 | Comparative Example 18 |
|---|---|---|
| 1. Esterification reaction product (Production Example 1) | 10.0 | — |
| 2. Liquid lanolin | 5.0 | 10.0 |
| 3. Polybutene | 5.0 | 10.0 |
| 4. Glyceryl (behenate/eicosadioate) | 2.0 | 2.0 |
| 5. Sucrose fatty acid ester | 3.0 | 3.0 |
| 6. Organic modified bentonite | 2.0 | 2.0 |
| 7. Diisostearyl malate | 10.0 | 10.0 |
| 8. 2-Ethylhexyl p-methoxycinnamate | 0.1 | 0.1 |
| 9. Antioxidant | 0.1 | 0.1 |
| 10. Trioctanoin | balance | balance |
| Total | 100.0 | 100.0 |

TABLE 36

| Sensory test | Example 17 | Comparative Example 18 |
|---|---|---|
| Effective length | ◎ | Δ |
| Gloss | ○ | ○ |
| Film-forming feeling | ◎ | Δ |

The followings were confirmed by the results shown in Table 36.

It was recognized that the eyegloss (paste type) of Example 17 was excellent in gloss and film-forming feeling (uniformity of cosmetic film), and the makeup was maintained for a long time. In addition, the eyegloss (paste type) of Example 17 was superior to the eyegloss (paste type) of Comparative Example 18 in both the gloss and film-forming feeling. Furthermore, the makeup was maintained for a longer time.

Example 18 and Comparative Example 19

Production of Powder Cheek Rouge

Powder cheek rouge having the formula shown in Table 37 was produced by the following process.

Raw materials 3 to 8 were uniformly mixed and dispersed to obtain mixture (A). Then, raw materials 1 and 2 were added to mixture (A), and the resulting mixture was pulverized and compression molded into a plate to obtain powder cheek rouge. The results of sensory evaluation are shown in Table 38.

TABLE 37

| Raw material | Example 18 | Comparative Example 19 |
|---|---|---|
| 1. Esterification reaction product (Production Example 2) | 7.0 | — |
| 2. Liquid lanolin | — | 7.0 |
| 3. Talc | 60.0 | 60.0 |
| 4. Mica | 10.9 | 10.9 |
| 5. Red No. 226 | 2.0 | 2.0 |
| 6. Boron nitride powder | 15.0 | 15.0 |
| 7. Nylon powder | 5.0 | 5.0 |
| 8. Preservative | 0.1 | 0.1 |
| Total | 100.0 | 100.0 |

TABLE 38

| Sensory test | Example 18 | Comparative Example 19 |
|---|---|---|
| Effective length | ◎ | Δ |
| Adhesion | ○ | Δ |
| Spread | ◎ | ○ |

The followings were confirmed by the results shown in Table 38.

It was recognized that the powder cheek rouge of Example 18 well adhered and spread on skin, and the makeup was maintained for a long time. In addition, the powder cheek rouge of Example 18 was superior to the powder cheek rouge of Comparative Example 19 in both the adhesion and spread. Furthermore, the makeup was maintained for a longer time.

Example 19 and Comparative Example 20

Production of Base Coat

Base coat having the formula shown in Table 39 was produced by the following process.

Raw materials 1 to 5 were uniformly mixed to obtain mixture (A). Then, raw materials 6 to 8 were added to mixture (A), and the resulting mixture was uniformly mixed to obtain base coat. The results of sensory evaluation are shown in Table 40.

TABLE 39

| Raw material | Example 19 | Comparative Example 20 |
|---|---|---|
| 1. Esterification reaction product (Production Example 1) | 5.0 | — |
| 2. Diisostearyl malate | — | 5.0 |
| 3. Isopropyl alcohol | 5.5 | 5.5 |
| 4. Butyl acetate | 35.0 | 35.0 |
| 5. Ethyl acetate | 30.0 | 30.0 |
| 6. Alkyl acrylate/styrene copolymer | 6.5 | 6.5 |
| 7. Sucrose benzoate ester | 13.0 | 13.0 |
| 8. Toluene sulfonamide resin | 5.0 | 5.0 |
| Total | 100.0 | 100.0 |

TABLE 40

| Sensory test | Example 19 | Comparative Example 20 |
|---|---|---|
| Effective length | ◎ | ○ |
| Gloss | ○ | Δ |
| Film-forming feeling | ◎ | Δ |

The followings were confirmed by the results shown in Table 40.

Base coats are applied to nails previous to the application of manicure products and planarize the nail surfaces to allow the manicure products to spread well. It was recognized that the base coat of Example 19 improved the gloss and film-forming feeling of a manicure product, and such effects were maintained for a long time. In addition, the base coat of Example 19 was superior to the base coat of Comparative Example 20 in both the gloss and film-forming feeling. Furthermore, the gloss was maintained for a longer time.

Example 20 and Comparative Example 21

Production of Top Coat

Top coat having the formula shown in Table 41 was produced by the following process.

Raw materials 1 to 5 were uniformly mixed to obtain mixture (A). Then, raw materials 6 to 9 were added to mixture (A), and the resulting mixture was uniformly mixed to obtain top coat. The results of sensory evaluation are shown in Table 42.

TABLE 41

| Raw material | Example 20 | Comparative Example 21 |
| --- | --- | --- |
| 1. Esterification reaction product (Production Example 2) | 8.0 | — |
| 2. Esterification reaction product (Production Example 3) | — | 8.0 |
| 3. Isopropyl alcohol | 5.0 | 5.0 |
| 4. Butyl acetate | 35.0 | 35.0 |
| 5. Ethyl acetate | 30.0 | 30.0 |
| 6. Alkyl acrylate/styrene copolymer | 3.0 | 3.0 |
| 7. Sucrose benzoate ester | 7.0 | 7.0 |
| 8. Toluene sulfonamide resin | 2.0 | 2.0 |
| 9. Nitrocellulose | 10.0 | 10.0 |
| Total | 100.0 | 100.0 |

TABLE 42

| Sensory test | Example 20 | Comparative Example 21 |
| --- | --- | --- |
| Effective length | ◎ | ○ |
| Shine | ○ | Δ |
| Adhesion | ◎ | ○ |

The followings were confirmed by the results shown in Table 42.

Top coats are applied on manicure products to improve the shine of the manicure products and keep the effects of the manicure products. It was recognized that the top coat of Example 20 applied on a manicure product improved the shine of the manicure product and kept the effects of the manicure product for a long time. In addition, it was recognized that the top coat of Example 20 was superior to the top coat of Comparative Example 21 in improvement of the shine and adhesion. Furthermore, the shine was maintained for a longer time.

Example 21 and Comparative Example 22

Production of Nail Enamel

Nail enamel having the formula shown in Table 43 was produced by the following process.

Raw materials 7 and 4 were mixed to raw material 1 or 2, and the resulting mixture was kneaded well. Then, other raw materials were added thereto, and the resulting mixture was uniformly dispersed to obtain nail enamel. The results of sensory evaluation are shown in Table 44.

TABLE 43

| Raw material | Example 21 | Comparative Example 22 |
| --- | --- | --- |
| 1. Esterification reaction product (Production Example 1) | 5.0 | — |
| 2. Castor oil | — | 5.0 |
| 3. Nitrocellulose | 10.0 | 10.0 |
| 4. Alkyd resin | 10.0 | 10.0 |
| 5. Ethyl acetate | 25.0 | 25.0 |
| 6. Butyl acetate | 40.0 | 40.0 |
| 7. Ethyl alcohol | 5.0 | 5.0 |
| 8. Titanium oxide-coated mica | 2.0 | 2.0 |
| 9. Red No. 202 | 1.0 | 1.0 |
| 10. Black iron oxide | 1.0 | 1.0 |
| 11. Yellow iron oxide | 0.5 | 0.5 |
| 12. Red No. 228 | 0.5 | 0.5 |
| Total | 100.0 | 100.0 |

TABLE 44

| Sensory test | Example 21 | Comparative Example 22 |
| --- | --- | --- |
| Clinginess | ◎ | ○ |
| Smoothness | ◎ | Δ |
| Shine | ◎ | Δ |
| Adhesion | ◎ | Δ |

The followings were confirmed by the results shown in Table 44.

It was recognized that the nail enamel of Example 21 readily clung to nails, was excellent in smoothness and shine, reduced the roughness of nails, and showed good adhesion. In addition, the effects of the nail enamel of Example 21 were higher than those of the nail enamel of Comparative Example 22.

Example 22 and Comparative Example 23

Production of Cleansing Cream

Cleansing cream having the formula shown in Table 45 was produced by the following process.

Raw materials 1 to 8 were mixed and dissolved by heating to 70° C. to obtain mixture (A). At the same time, raw materials 9 to 13 were mixed and heated to 70° C. to obtain mixture (B). Mixture (A) was gradually added to mixture (B) while stirring at 70° C. for saponification reaction. After the completion of the saponification reaction, the mixture was cooled while stirring to obtain cleansing cream. The results of sensory evaluation are shown in Table 46.

TABLE 45

| Raw material | Example 22 | Comparative Example 23 |
| --- | --- | --- |
| 1. Esterification reaction product (Production Example 2) | 1.0 | — |
| 2. Polyglyceryl-2 triisostearate | — | 1.0 |
| 3. Lauric acid | 5.0 | 5.0 |
| 4. Myristic acid | 10.0 | 10.0 |
| 5. Palmitic acid | 10.0 | 10.0 |
| 6. Stearic acid | 5.0 | 5.0 |
| 7. Oleyl alcohol | 1.5 | 1.5 |
| 8. High-polymerized dimethylpolysiloxane | 0.1 | 0.1 |
| 9. Glycerin | 18.0 | 18.0 |
| 10. Potassium hydroxide | 6.0 | 6.0 |
| 11. Preservative | 0.5 | 0.5 |

TABLE 45-continued

| Raw material | Example 22 | Comparative Example 23 |
|---|---|---|
| 12. Perfume | 0.1 | 0.1 |
| 13. Purified water | balance | balance |
| Total | 100.0 | 100.0 |

TABLE 46

| Sensory test | Example 22 | Comparative Example 23 |
|---|---|---|
| Softness | ◎ | Δ |
| Moisturizing properties | ◎ | ○ |
| Creaminess | ◎ | Δ |
| Cleansing properties | ◎ | ○ |

The followings were confirmed by the results shown in Table 46.

It was recognized that the cleansing cream of Example was excellent in cleansing properties, and softened, moisturized, and smoothened skin. Furthermore, these effects of the cleansing cream of Example 22 were higher than those of the cleansing cream of Comparative Example 23.

Example 23 and Comparative Example 24

Preparation of Cleansing Oil

Cleansing oil having the formula shown in Table 47 was produced by the following process.

Raw materials 1 to 7 were uniformly mixed to obtain cleansing oil. The results of sensory evaluation are shown in Table 48.

TABLE 47

| Raw material | Example 23 | Comparative Example 24 |
|---|---|---|
| 1. Esterification reaction product (Production Example 1) | 3.0 | — |
| 2. Liquid lanolin | — | 3.0 |
| 3. Trioctanoin | 20.0 | 20.0 |
| 4. Cetyl 2-ethylhexanoate | 32.0 | 32.0 |
| 5. Liquid paraffin | 40.9 | 40.9 |
| 6. POE-Sorbit tetraoleate (30 E.O.) | 4.0 | 4.0 |
| 7. Perfume | 0.1 | 0.1 |
| Total | 100.0 | 100.0 |

TABLE 48

| Sensory test | Example 23 | Comparative Example 24 |
|---|---|---|
| Softness | ◎ | ○ |
| Moisturizing properties | ◎ | ○ |
| Creaminess | ◎ | Δ |
| Cleansing properties | ◎ | ○ |

The followings were confirmed by the results shown in Table 48.

It was recognized that the cleansing oil of Example 23 was excellent in cleansing properties, and softened, moisturized, and smoothened skin. Furthermore, these effects of the cleansing oil of Example 23 were higher than those of the cleansing oil of Comparative Example 24.

Example 24 and Comparative Example 25

Production of Cleansing Cream

Cleansing cream having the formula shown in Table 49 was produced by the following process.

Raw materials 1 to 9 were dissolved by heating and uniformly mixed to obtain mixture (A). At the same time, raw materials 10 to 15 were heated and uniformly mixed to obtain mixture (B). Mixture (B) was added to mixture (A) at 80° C. for emulsification and then cooled to obtain cleansing cream. The results of sensory evaluation are shown in Table 50.

TABLE 49

| Raw material | Example 24 | Comparative Example 25 |
|---|---|---|
| 1. Esterification reaction product (Production Example 2) | 8.0 | — |
| 2. Esterification reaction product (Production Example 3) | — | 8.0 |
| 3. Stearic acid | 5.0 | 5.0 |
| 4. Cetyl alcohol | 2.0 | 2.0 |
| 5. Sorbitan sesquioleate | 1.0 | 1.0 |
| 6. POE-sorbitan monooleate (20 E.O.) | 2.0 | 2.0 |
| 7. Dimethyl polysiloxane | 0.5 | 0.5 |
| 8. Squalane | 15.0 | 15.0 |
| 9. Trioctanoin | 5.0 | 5.0 |
| 10. Glycerin | 5.0 | 5.0 |
| 11. 1,3-Butylene glycol | 10.0 | 10.0 |
| 12. Sodium hydroxide | 0.7 | 0.7 |
| 13. Preservative | 0.5 | 0.5 |
| 14. Perfume | 0.1 | 0.1 |
| 15. Purified water | balance | balance |
| Total | 100.0 | 100.0 |

TABLE 50

| Sensory test | Example 24 | Comparative Example 25 |
|---|---|---|
| Softness | ◎ | Δ |
| Moisturizing properties | ◎ | ○ |
| Smoothness | ◎ | Δ |
| Cleansing properties | ◎ | Δ |

The followings were confirmed by the results shown in Table 50.

It was recognized that the cleansing cream of Example 24 was excellent in cleansing properties, and softened, moisturized, and smoothened skin. Furthermore, these effects of the cleansing cream of Example 24 were higher than those of the cleansing cream of Comparative Example 25.

Example 25 and Comparative Example 26

Production of Lotion

Lotion having the formula shown in Table 51 was produced by the following process.

Raw materials 1 to 4 were uniformly mixed and dissolved to obtain mixture (A). At the same time, raw materials 5 to 9 were uniformly mixed and dissolved to obtain mixture (B). Then, mixture (A) was added to mixture (B) while stirring to obtain lotion. The results of sensory evaluation are shown in Table 52.

TABLE 51

| Raw material | Example 25 | Comparative Example 26 |
|---|---|---|
| 1. Esterification reaction product (Production Example 2) | 0.5 | — |
| 2. Liquid lanolin | — | 0.5 |
| 3. Ethyl alcohol | 5.0 | 5.0 |
| 4. POE-hydrogenated castor oil (60 E.O.) | 1.0 | 1.0 |
| 5. Glycerin | 3.0 | 3.0 |
| 6. 1,3-Butylene glycol | 10.0 | 10.0 |
| 7. Alkyl-modified carboxyvinyl polymer | 0.01 | 0.01 |
| 8. Preservative | 0.5 | 0.5 |
| 9. Purified water | balance | balance |
| Total | 100.0 | 100.0 |

TABLE 52

| Sensory test | Example 25 | Comparative Example 26 |
|---|---|---|
| Softness | ◎ | Δ |
| Moisturizing properties | ◎ | ○ |
| Smoothness | ○ | Δ |

The followings were confirmed by the results shown in Table 52.

It was recognized that the lotion of Example 25 softened, moisturized, and smoothened skin. Furthermore, these effects of the lotion of Example 25 were higher than those of the lotion of Comparative Example 26.

Example 26 and Comparative Example 27

Production of Serum

Serum having the formula shown in Table 53 was produced by the following process.

Raw materials 1 to 5 were mixed and dissolved to obtain mixture (A). Raw materials 6 to 11 were mixed and heated to 80° C. to obtain mixture (B). Mixture (B) was added to mixture (A), and the resulting mixture was treated with a homomixer and then cooled to obtain serum. The results of sensory evaluation are shown in Table 54.

TABLE 53

| Raw material | Example 26 | Comparative Example 27 |
|---|---|---|
| 1. Esterification reaction product (Production Example 1) | 2.0 | — |
| 2. Trioctanoin | — | 2.0 |
| 3. Sorbitan sesquioleate | 0.1 | 0.1 |
| 4. POE-sorbitan monooleate (20 E.O.) | 0.5 | 0.5 |
| 5. Cetyl 2-ethylhexanoate | 5.0 | 5.0 |
| 6. Ethyl alcohol | 10.0 | 10.0 |
| 7. Dipropylene glycol | 10.0 | 10.0 |
| 8. Glycerin | 10.0 | 10.0 |
| 9. Perfume | 0.1 | 0.1 |
| 10. Preservative | 0.1 | 0.1 |
| 11. Purified water | balance | balance |
| Total | 100.0 | 100.0 |

TABLE 54

| Sensory test | Example 26 | Comparative Example 27 |
|---|---|---|
| Spread | ◎ | ○ |
| Moisturizing properties | ◎ | Δ |
| Softness | ◎ | Δ |

The followings were confirmed by the results shown in Table 54.

It was recognized that the serum of Example 26 was well spread on skin and softened it, and moisturized the skin for a long time. In addition, these effects of the serum of Example 26 were higher than those of the serum of Comparative Example 27.

Example 27 and Comparative Example 28

Production of Milky Lotion

Milky lotion having the formula shown in Table 55 was produced by the following process.

Raw materials 1 to 6 were mixed and dissolved at 80° C. to obtain mixture (A). At the same time, raw materials 7 to 12 were mixed and heated to 80° C. and were added to mixture (A). The resulting mixture was treated with a homomixer and then cooled to obtain milky lotion. The results of sensory evaluation are shown in Table 56.

TABLE 55

| Raw material | Example 27 | Comparative Example 28 |
|---|---|---|
| 1. Esterification reaction product (Production Example 1) | 10.0 | — |
| 2. Lanolin | — | 10.0 |
| 3. Liquid paraffin | 20.0 | 20.0 |
| 4. Cetyl alcohol | 0.5 | 0.5 |
| 5. Stearoyl glutamate | 1.0 | 1.0 |
| 6. Glyceryl monostearate | 3.0 | 3.0 |
| 7. Dipropylene glycol | 10.0 | 10.0 |
| 8. Glycerin | 5.0 | 5.0 |
| 9. Carboxyvinyl polymer | 0.05 | 0.05 |
| 10. Preservative | 0.1 | 0.1 |
| 11. Sodium hydroxide | proper quantity | proper quantity |
| 12. Purified water | balance | balance |
| Total | 100.0 | 100.0 |

TABLE 56

| Sensory test | Example 27 | Comparative Example 28 |
|---|---|---|
| Spread | ◎ | Δ |
| Moisturizing properties | ◎ | ○ |
| Softness | ◎ | Δ |

The followings were confirmed by the results shown in Table 56.

It was recognized that the milky lotion of Example 27 was well spread on and softened skin and moisturized the skin for a long time. Furthermore, these effects of the milky lotion of Example 27 were higher than those of the milky lotion of Comparative Example 28.

Example 28 and Comparative Example 29

Production of Emollient Cream (W/O Type)

Emollient cream (W/O type) having the formula shown in Table 57 was produced by the following process.

Raw material 1 and raw material 2 or 3 were mixed at room temperature to obtain mixture (A). At the same time, raw materials 4 to 8 were uniformly dissolved while heating to 80° C., and then mixture (A) was gradually added thereto and uniformly dispersed to obtain mixture (B). Then, raw materials 9 and 10 were heated to 70° C. and were added to mixture (B) while emulsifying the mixture with a homomixer. Then, deaeration, filtration, and cooling were conducted to obtain emollient cream (W/O type). The results of sensory evaluation are shown in Table 58.

TABLE 57

| Raw material | Example 28 | Comparative Example 29 |
| --- | --- | --- |
| 1. 1% Sodium alginate aqueous solution | 10.0 | 10.0 |
| 2. Esterification reaction product (Production Example 1) | 3.0 | — |
| 3. Esterification reaction product (Production Example 3) | — | 3.0 |
| 4. Ceresin | 1.0 | 1.0 |
| 5. Beeswax | 2.0 | 2.0 |
| 6. Vaseline | 5.0 | 5.0 |
| 7. Squalane | 32.0 | 32.0 |
| 8. Liquid paraffin | 10.0 | 10.0 |
| 9. Glycerin | 2.0 | 2.0 |
| 10. Purified water | 35.0 | 35.0 |
| Total | 100.0 | 100.0 |

TABLE 58

| Sensory test | Example 28 | Comparative Example 29 |
| --- | --- | --- |
| Spread | ◎ | ◎ |
| Moisturizing properties | ◎ | ○ |
| Softness | ◎ | ○ |

The followings were confirmed by the results shown in Table 58.

It was recognized that the effects of spread, moisturizing properties, and softness were imparted to the emollient cream of Example 28 and the emollient cream of Comparative Example 29, and these effects of the emollient cream of Example 28 were higher than those of the cleansing cream of Comparative Example 29.

Example 29 and Comparative Example 30

Production of Vitamin C Derivative-Containing Cream

Vitamin C derivative-containing cream having the formula shown in Table 59 was produced by the following process.

Raw materials 1 to 3 were uniformly mixed to obtain mixture (A). At the same time, raw materials 4 to 9 were uniformly mixed to obtain mixture (B). Then, mixture (B) was added to mixture (A) and emulsified to obtain vitamin C derivative-containing cream. The results of sensory evaluation are shown in Table 60.

TABLE 59

| Raw material | Example 29 | Comparative Example 30 |
| --- | --- | --- |
| 1. Esterification reaction product (Production Example 1) | 5.0 | — |
| 2. Organic modified hectorite | 1.5 | 1.5 |
| 3. Trioctanoin | 25.0 | 30.0 |
| 4. Magnesium-L-ascorbyl-phosphate | 3.0 | 3.0 |
| 5. Sodium citrate | 1.0 | 1.0 |
| 6. 1,3-Butylene glycol | 3.0 | 3.0 |
| 7. Preservative | 0.5 | 0.5 |
| 8. Perfume | 0.1 | 0.1 |
| 9. Purified water | balance | balance |
| Total | 100.0 | 100.0 |

TABLE 60

| Sensory test | Example 29 | Comparative Example 30 |
| --- | --- | --- |
| Moisturizing properties | ◎ | ○ |
| Adhesion | ◎ | Δ |
| Softness | ○ | ○ |
| Film-forming feeling | ◎ | Δ |

The followings were confirmed by the results shown in Table 60.

It was recognized that the vitamin C derivative-containing cream of Example 29 well moistured, adhered to, and softened skin and that film-forming feeling was maintained for a long time, and that these effects of the vitamin C derivative-containing cream of Example 29 were higher than those of the vitamin C derivative-containing cream of Comparative Example 30.

Example 30 and Comparative Example 31

Production of Eye Cream

Eye cream having the formula shown in Table 61 was produced by the following process.

Raw materials 1 to 8 were mixed and dissolved at 80° C. to obtain mixture (A). Then, raw materials 9 to 14 were mixed and heated to 80° C. and then added to mixture (A). The resulting mixture was treated with a homomixer and then cooled to obtain eye cream. The results of sensory evaluation are shown in Table 62.

TABLE 61

| Raw material | Example 30 | Comparative Example 31 |
| --- | --- | --- |
| 1. Esterification reaction product (Production Example 2) | 1.5 | — |
| 2. Polybutene | — | 1.5 |
| 3. Sorbitan tristearate | 0.05 | 0.05 |
| 4. POE-Sorbitan trioleate (20 E.O.) | 0.1 | 0.1 |
| 5. Di(phytosteryl/behenyl/octyldodecyl) N-lauroyl-L-glutamate | 0.5 | 0.5 |
| 6. Microcrystalline wax | 0.5 | 0.5 |
| 7. Stearyl alcohol | 2.5 | 2.5 |
| 8. Dimethyl polysiloxane | 0.5 | 0.5 |
| 9. Dipropylene glycol | 5.0 | 5.0 |
| 10. Glycerin | 5.0 | 5.0 |
| 11. Sodium alginate | 0.1 | 0.1 |
| 12. Preservative | 0.1 | 0.1 |
| 13. Perfume | 0.1 | 0.1 |
| 14. Purified water | balance | balance |
| Total | 100.0 | 100.0 |

TABLE 62

| Sensory test | Example 30 | Comparative Example 31 |
| --- | --- | --- |
| Spread | ◎ | Δ |
| Moisturizing feeling | ◎ | Δ |
| Softness | ◎ | Δ |

The followings were confirmed by the results shown in Table 62.

It was recognized that the eye cream of Example 30 was well spread on and softened skin and that moisturizing feeling was maintained for a long time. Furthermore, it was confirmed that these effects of the eye cream of Example 30 were higher than those of the eye cream of Comparative Example 31.

Example 31 and Comparative Example 32

Production of Conditioning Shampoo

Conditioning shampoo having the formula shown in Table 63 was produced by the following process.

Raw material 8 was added to raw material 12, and the mixture was heated to 70° C. while stirring, and other raw materials were added thereto. The resulting mixture was stirred and dissolved, and then cooled to obtain conditioning shampoo. The results of sensory evaluation are shown in Table 64.

TABLE 63

| Raw material | Example 31 | Comparative Example 32 |
|---|---|---|
| 1. Esterification reaction product (Production Example 2) | 2.5 | — |
| 2. Diisostearyl malate | — | 2.5 |
| 3. Lauryl polyoxyethylene (3) sulfate ester triethanolamine salt (30% aqueous solution) | 10.0 | 10.0 |
| 4. Lauryl polyoxyethylene (3) sulfate ester sodium salt (30% aqueous solution) | 20.0 | 20.0 |
| 5. Lauryl sulfate ester sodium salt (30% aqueous solution) | 5.0 | 5.0 |
| 6. Lauroyl diethanolamide | 3.0 | 3.0 |
| 7. Lauryldimethylaminoacetic acid betaine (30% aqueous solution) | 7.0 | 7.0 |
| 8. Cationated cellulose | 0.2 | 0.2 |
| 9. Perfume | 0.1 | 0.1 |
| 10. Preservative | 0.2 | 0.2 |
| 11. Sequestering agent, pH-adjuster | 1.0 | 1.0 |
| 12. Purified water | 51.0 | 51.0 |
| Total | 100.0 | 100.0 |

TABLE 64

| Sensory test | Example 31 | Comparative Example 32 |
|---|---|---|
| Moisturizing feeling | ◎ | ○ |
| Gloss | ○ | ○ |
| Softness | ◎ | ○ |
| Conditioning feeling | ◎ | △ |

The followings were confirmed by the results shown in Table 64.

It was recognized that the conditioning shampoo of Example 31 imparted moisturizing feeling, gloss, softness, and conditioning feeling to hair. In addition, it was confirmed that these effects of the conditioning shampoo of Example 31 were higher than those of the conditioning shampoo of Comparative Example 32.

Example 32 and Comparative Example 33

Production of Cuticle-protecting Gel

Cuticle-protecting gel having the formula shown in Table 65 was produced by the following process.

Raw materials 1 to 5 were uniformly mixed to obtain mixture (A). At the same time, raw materials 6 to 10 and 12 were uniformly mixed to obtain mixture (B). Then, mixtures (A) and (B) were mixed while adding mixture (A) to mixture (B), and then raw material 11 was added thereto. The resulting mixture was uniformly mixed to obtain cuticle-protecting gel. The results of sensory evaluation are shown in Table 66.

TABLE 65

| Raw material | Example 32 | Comparative Example 33 |
|---|---|---|
| 1. Esterification reaction product (Production Example 2) | 3.0 | — |
| 2. Diisostearyl malate | — | 3.0 |
| 3. Cetyl 2-ethylhexanoate | 10.0 | 10.0 |
| 4. Liquid paraffin | 9.0 | 9.0 |
| 5. Methylphenylpolysiloxane | 3.0 | 3.0 |
| 6. Alkyl-modified carboxyvinyl polymer | 0.1 | 0.1 |
| 7. Carboxymethyl cellulose | 0.5 | 0.5 |
| 8. Triethanolamine | 0.1 | 0.1 |
| 9. Propylene glycol | 10.0 | 10.0 |
| 10. Preservative | 1.0 | 1.0 |
| 11. Perfume | 0.1 | 0.1 |
| 12. Purified water | balance | balance |
| Total | 100.0 | 100.0 |

TABLE 66

| Sensory test | Example 32 | Comparative Example 33 |
|---|---|---|
| Softness | ◎ | △ |
| Moisturizing feeling | ◎ | ○ |
| Gloss | ◎ | △ |
| Conditioning feeling | ◎ | ○ |

The followings were confirmed by the results shown in Table 66.

It was recognized that the cuticle-protecting gel of Example 32 well softened and moistured hair and imparted gloss and conditioning feeling to the hair. Furthermore, these effects of the cuticle-protecting gel of Example 32 were higher than those of the cuticle-protecting gel of Comparative Example 33.

Example 33 and Comparative Example 34

Production of Hair Rinse

Hair rinse having the formula shown in Table 67 was produced by the following process.

Raw materials 1 to 5 were uniformly mixed and dissolved to obtain mixture (A). At the same time, raw materials 6 to 9 and 11 were uniformly mixed and dissolved to obtain mixture (B). Then, mixture (A) and mixture (B) were heated to 80° C. The mixture (A) was added to mixture (B) at 80° C. for emulsification, and then raw material 10 was mixed thereto to obtain hair rinse. The results of sensory evaluation are shown in Table 68.

TABLE 67

| Raw material | Example 33 | Comparative Example 34 |
|---|---|---|
| 1. Esterification reaction product (Production Example 1) | 1.5 | — |
| 2. Liquid lanolin | — | 1.5 |
| 3. Cetyl 2-ethylhexanoate | 10.0 | 10.0 |
| 4. Isononyl isononanoate | 5.0 | 5.0 |
| 5. Behenyl alcohol | 3.0 | 3.0 |
| 6. Distearyldimethylammonium chloride | 2.5 | 2.5 |
| 7. Highly polymerized methylpolysiloxane emulsion | 2.0 | 2.0 |
| 8. Hydroxyethyl cellulose | 0.2 | 0.2 |
| 9. Preservative | 1.0 | 1.0 |

TABLE 67-continued

| Raw material | Example 33 | Comparative Example 34 |
|---|---|---|
| 10. Perfume | 0.1 | 0.1 |
| 11. Purified water | balance | balance |
| Total | 100.0 | 100.0 |

TABLE 68

| Sensory test | Example 33 | Comparative Example 34 |
|---|---|---|
| Softness | ◉ | Δ |
| Moisturizing feeling | ◉ | ○ |
| Gloss | ○ | Δ |
| Conditioning feeling | ◉ | Δ |

The followings were confirmed by the results shown in Table 68.

It was recognized that the hair rinse of Example 33 well softened and moistured hair and imparted gloss and conditioning feeling to the hair. Furthermore, these effects of the hair rinse of Example 33 were higher than those of the hair rinse of Comparative Example 34.

Example 34 and Comparative Example 35

Production of Hair Conditioner

Hair conditioner having the formula shown in Table 69 was produced by the following process.

Raw materials 1 to 7 were uniformly mixed and dissolved to obtain mixture (A). At the same time, raw materials 8 to and 13 were uniformly mixed and dissolved to obtain mixture (B). Then, mixture (A) and mixture (B) were heated to 80° C., and then mixture (A) was added to mixture (B) at 80° C. for emulsification. Then, raw material 12 was mixed thereto to obtain hair conditioner. The results of sensory evaluation are shown in Table 70.

TABLE 69

| Raw material | Example 34 | Comparative Example 35 |
|---|---|---|
| 1. Esterification reaction product (Production Example 2) | 2.0 | — |
| 2. Diisostearyl malate | — | 2.0 |
| 3. Trioctanoin | 3.0 | 3.0 |
| 4. Methylphenylpolysiloxane | 1.0 | 1.0 |
| 5. Dimethyl polysiloxane | 2.0 | 2.0 |
| 6. Stearyl alcohol | 1.0 | 1.0 |
| 7. Cetyl alcohol | 0.5 | 0.5 |
| 8. Cetyltrimethylammonium chloride | 1.0 | 1.0 |
| 9. 1,3-Butylene glycol | 7.0 | 7.0 |
| 10. Cationated cellulose | 0.2 | 0.2 |
| 11. Preservative | 1.0 | 1.0 |
| 12. Perfume | 0.1 | 0.1 |
| 13. Purified water | balance | balance |
| Total | 100.0 | 100.0 |

TABLE 70

| Sensory test | Example 34 | Comparative Example 35 |
|---|---|---|
| Softness | ◉ | ○ |
| Moisturizing feeling | ◉ | ○ |
| Gloss | ◉ | Δ |
| Conditioning feeling | ◉ | Δ |

The followings were confirmed by the results shown in Table 70.

It was recognized that the hair conditioner of Example well softened and moistured hair and imparted gloss and conditioning feeling to the hair. Furthermore, these effects of the hair conditioner of Example 34 were higher than those of the hair conditioner of Comparative Example 35.

Example 35 and Comparative Example 36

Production of Hair Cream

Hair cream having the formula shown in Table 71 was produced by the following process.

Raw materials 1 to 5 were uniformly mixed and dissolved to obtain mixture (A). Raw materials 6 to 10 and 12 were uniformly mixed and dissolved to obtain mixture (B). Then, mixture (A) and mixture (B) were heated to 80° C., and then mixture (B) was added to mixture (A) at 80° C. for emulsification. Then, raw material 11 was added thereto, and the resulting mixture was cooled to obtain hair cream. The results of sensory evaluation are shown in Table 72.

TABLE 71

| Raw material | Example 35 | Comparative Example 36 |
|---|---|---|
| 1. Esterification reaction product (Production Example 1) | 3.0 | — |
| 2. Esterification reaction product (Production Example 3) | — | 3.0 |
| 3. Dimethyl polysiloxane | 5.0 | 5.0 |
| 4. Liquid paraffin | 9.0 | 9.0 |
| 5. Cetyl 2-ethylhexanoate | 13.0 | 13.0 |
| 6. Behenyl alcohol | 4.0 | 4.0 |
| 7. POE-oleyl ether | 1.0 | 1.0 |
| 8. Propylene glycol | 7.0 | 7.0 |
| 9. Pyrrolidone carboxylate sodium salt | 0.5 | 0.5 |
| 10. Preservative | 0.5 | 0.5 |
| 11. Perfume | 0.1 | 0.1 |
| 12. Purified water | balance | balance |
| Total | 100.0 | 100.0 |

TABLE 72

| Sensory test | Example 35 | Comparative Example 36 |
|---|---|---|
| Softness | ◉ | Δ |
| Moisturizing feeling | ◉ | ○ |
| Gloss | ○ | Δ |
| Conditioning feeling | ◉ | Δ |

The followings were confirmed by the results shown in Table 72.

It was recognized that the hair cream of Example 35 well softened and moistured hair and imparted gloss and conditioning feeling to the hair. Furthermore, these effects of the hair cream of Example 35 were higher than those of the hair cream of Comparative Example 36.

Example 36 and Comparative Example 37

Production of Hair Wax

Hair wax having the formula shown in Table 73 was produced by the following process.

Raw materials 1 to 9 were uniformly mixed and dissolved to obtain mixture (A). At the same time, raw materials 10, 11, 13, and 14 were uniformly mixed and dissolved to obtain mixture (B). Then, mixture (A) and mixture (B) were heated to 80° C., and then mixture (A) was added to mixture (B) at 80° C. for emulsification. Then, raw material 12 was mixed thereto to obtain hair wax. The results of sensory evaluation are shown in Table 74.

TABLE 73

| Raw material | Example 36 | Comparative Example 37 |
|---|---|---|
| 1. Esterification reaction product (Production Example 2) | 2.0 | — |
| 2. Diisostearyl malate | — | 2.0 |
| 3. Candelilla wax | 3.0 | 3.0 |
| 4. Paraffin wax | 10.0 | 10.0 |
| 5. Polyoxyethylene (10) oleyl alcohol | 3.0 | 3.0 |
| 6. Steary alcohol | 0.5 | 0.5 |
| 7. Liquid paraffin | 8.0 | 8.0 |
| 8. Squalane | 8.0 | 8.0 |
| 9. Glycerin fatty acid ester eicosadioate condensate | 1.0 | 1.0 |
| 10. 1,3-Butylene glycol | 5.0 | 5.0 |
| 11. Sodium hydroxide | 0.1 | 0.1 |
| 12. Perfume | 0.1 | 0.1 |
| 13. Decaglycerin fatty acid ester eicosadioate condensate | 0.5 | 0.5 |
| 14. Purified water | balance | balance |
| Total | 100.0 | 100.0 |

TABLE 74

| Sensory test | Example 36 | Comparative Example 37 |
|---|---|---|
| Softness | ◉ | ○ |
| Moisturizing feeling | ◉ | ○ |
| Gloss | ◉ | Δ |
| Conditioning feeling | ◉ | X |

The followings were confirmed by the results shown in Table 74.

It was recognized that the hair wax of Example 36 well softened and moistured hair and imparted gloss and conditioning feeling to the hair. Furthermore, these effects of the hair wax of Example 36 were higher than those of the hair wax of Comparative Example 37.

Example 37 and Comparative Example 38

Production of Multi-Phase Emulsion Sunscreen (W/O Type)

Multi-phase emulsion sunscreen (W/O type) having the formula shown in Table 75 was produced by the following process.

Raw materials 1 to 12 were uniformly mixed to obtain mixture (A). At the same time, raw materials 13 to 16 were uniformly mixed to obtain mixture (B). Then, mixture (B) was added to mixture (A) for emulsification. The resulting emulsion was put into a resin bottle in which a stainless steel ball was placed to obtain multi-phase emulsion sunscreen (W/O type). The results of sensory evaluation are shown in Table 76.

TABLE 75

| Raw material | Example 37 | Comparative Example 38 |
|---|---|---|
| 1. Esterification reaction product (Production Example 1) | 12.0 | — |
| 2. Lanolin | — | 12.0 |

TABLE 75-continued

| Raw material | Example 37 | Comparative Example 38 |
|---|---|---|
| 3. Stearic acid-treated titanium oxide microparticle | 10.0 | 10.0 |
| 4. Decamethylcyclopentasiloxane | 15.0 | 15.0 |
| 5. 2-Ethylhexyl p-methoxycinnamate | 5.0 | 5.0 |
| 6. Neopentyl glycol dicaprate | 9.8 | 9.8 |
| 7. Trimethoxycinnamic acid | 2.0 | 2.0 |
| 8. Cetyl dimethicone copolyol | 3.0 | 3.0 |
| 9. POE-sorbitan monooleate (20 E.O.) | 0.2 | 0.2 |
| 10. Sorbitan sesquioleate | 0.8 | 0.8 |
| 11. Nylon powder | 2.0 | 2.0 |
| 12. Perfume | 0.1 | 0.1 |
| 13. Ethyl alcohol | 5.0 | 5.0 |
| 14. Sodium chloride | 0.1 | 0.1 |
| 15. 1,3-Butylene glycol | 5.0 | 5.0 |
| 16. Purified water | balance | balance |
| Total | 100.0 | 100.0 |

TABLE 76

| Sensory test | Example 37 | Comparative Example 38 |
|---|---|---|
| Effective length | ◉ | Δ |
| Adhesion | ◉ | Δ |
| Film-forming feeling | ◉ | ○ |

The followings were confirmed by the results shown in Table 76.

It was recognized that the multi-phase emulsion sunscreen (W/O type) of Example 37 was excellent in adhesion to skin and film-forming feeling (uniformity of cosmetic film), and the makeup was maintained for a long time. The multi-phase emulsion sunscreen (W/O type) of Example 37 was excellent in both the adhesion and the film-forming feeling compared to those of the multi-phase emulsion sunscreen (W/O type) of Comparative Example 38, and the makeup was maintained for a longer time.

Example 38 and Comparative Example 39

Production of Sunscreen Cream (O/W Type)

Sunscreen cream (O/W type) having the formula shown in Table 77 was produced by the following process.

Raw materials 1 to 11 were heated to 70° C. and uniformly mixed to obtain mixture (A). At the same time, raw materials 13 to 17 were heated to 70° C. and uniformly mixed to obtain mixture (B). Then, mixture (B) was added to mixture (A), and the resulting mixture was emulsified. The resulting emulsion was cooled to room temperature, and then raw material 12 was mixed thereto to obtain sunscreen cream (O/W type). The results of sensory evaluation are shown in Table 78.

TABLE 77

| Raw material | Example 38 | Comparative Example 39 |
|---|---|---|
| 1. Esterification reaction product (Production Example 2) | 10.0 | — |
| 2. Polyglyceryl-2 triisostearate | — | 10.0 |
| 3. Titanium oxide | 10.0 | 10.0 |
| 4. Cetyl 2-ethylhexanoate | 7.0 | 7.0 |
| 5. Liquid paraffin | 3.0 | 3.0 |
| 6. POE-sorbitan monooleate (20 E.O.) | 0.7 | 0.7 |
| 7. Sorbitan sesquioleate | 0.3 | 0.3 |
| 8. Stearic acid | 1.0 | 1.0 |

TABLE 77-continued

| Raw material | Example 38 | Comparative Example 39 |
|---|---|---|
| 9. Cetostearyl alcohol | 1.0 | 1.0 |
| 10. Glyceryl monostearate | 1.0 | 1.0 |
| 11. Hydrogenated soybean phospholipid | 0.5 | 0.5 |
| 12. Perfume | 0.1 | 0.1 |
| 13. Sodium hydroxide | 0.15 | 0.15 |
| 14. 1,3-Butylene glycol | 10.0 | 10.0 |
| 15. Preservative | 0.3 | 0.3 |
| 16. Xanthan gum | 0.2 | 0.2 |
| 17. Purified water | balance | balance |
| Total | 100.0 | 100.0 |

TABLE 78

| Sensory test | Example 38 | Comparative Example 39 |
|---|---|---|
| Effective length | ◎ | Δ |
| Adhesion | ◎ | Δ |
| Film-forming feeling | ◎ | Δ |

The followings were confirmed by the results shown in Table 78.

It was recognized that the sunscreen cream (O/W type) of Example 38 was excellent in adhesion to skin and film-forming feeling (uniformity of cosmetic film), and the makeup was maintained for a long time. The sunscreen cream (O/W type) of Example 38 was excellent in both adhesion and film-forming feeling compared to those of the sunscreen cream (O/W type) of Comparative Example 39, and the makeup was maintained for a longer time.

Example 39 and Comparative Example 40

Production of Sunscreen Milky Lotion (W/O Type)

Sunscreen milky lotion (W/O type) having the formula shown in Table 79 was produced by the following process.

Raw materials 1 and 5 were mixed and heated for dissolving raw material 5, and raw materials 2 to 4 and 6 to 16 were added thereto. The resulting mixture was uniformly mixed to obtain mixture (A). At the same time, raw materials 17 and 18 were uniformly mixed to obtain mixture (B). Then, mixture (B) was added to mixture (A), and the resulting mixture was emulsified to obtain sunscreen milky lotion (W/O type). The results of sensory evaluation are shown in Table 80.

TABLE 79

| Raw material | Example 39 | Comparative Example 40 |
|---|---|---|
| 1. Esterification reaction product (Production Example 1) | 12.0 | — |
| 2. Lanolin | — | 12.0 |
| 3. Octyl paramethoxycinnamate | 5.0 | 5.0 |
| 4. Oxybenzone | 3.0 | 3.0 |
| 5. 4-tert-Butyl-4'-methoxydibenzoylmethane | 2.0 | 2.0 |
| 6. Hydrophobicized titanium dioxide | 5.0 | 5.0 |
| 7. Hydrophobicized zinc oxide | 5.0 | 5.0 |
| 8. Squalane | 20.0 | 20.0 |
| 9. Isononyl isononanoate | 5.0 | 5.0 |
| 10. Silicone oil | 5.0 | 5.0 |
| 11. Silicone resin | 2.0 | 2.0 |
| 12. Glycerin diisostearate | 2.0 | 2.0 |
| 13. Poly(oxyethylene/oxypropylene) methylpolysiloxane copolymer | 0.5 | 0.5 |
| 14. Decaglycerin fatty acid ester eicosadioate condensate | 0.5 | 0.5 |
| 15. Preservative | 0.1 | 0.1 |
| 16. Perfume | 0.1 | 0.1 |
| 17. 1,3-Butylene glycol | 5.0 | 5.0 |
| 18. Purified water | balance | balance |
| Total | 100.0 | 100.0 |

TABLE 80

| Sensory test | Example 39 | Comparative Example 40 |
|---|---|---|
| Effective length | ◎ | Δ |
| Adhesion | ◎ | Δ |
| Film-forming feeling | ◎ | ○ |

The followings were confirmed by the results shown in Table 80.

It was recognized that the sunscreen milky lotion (W/O type) of Example 39 was excellent in adhesion to skin and film-forming feeling (uniformity of cosmetic film), and the makeup was maintained for a long time. These effects of the sunscreen milky lotion (W/O type) of Example 39 were higher than those of the sunscreen milky lotion (W/O type) of Comparative Example 40, and the makeup was maintained for a longer time. In addition, it was confirmed that the solubility of 4-tert-butyl-4'-methoxydibenzoylmethane, which has low solubility, was improved by being mixed with an esterification reaction product (Production Example 1).

Examples 40 to 42 and Comparative Example 41

Production of Sunscreen Cream (W/O Type)

Sunscreen cream (W/O type) having the formula shown in Table 81 was produced by the following process.

Raw materials 1 to 7 were uniformly mixed to obtain mixture (A). At the same time, raw materials 8 to 11 were uniformly mixed to obtain mixture (B). Then, mixture (B) was added to mixture (A), and the resulting mixture was emulsified to obtain sunscreen cream (W/O type). The results of sensory evaluation are shown in Table 82. In this embodiment, the SPF value was measured with UV-1000F manufactured by LabSphere Inc. in order to evaluate ultraviolet-protection effect as sunscreen. The obtained SPF values were assessed according to the following evaluation criteria, and samples satisfying the criteria represented by ○ were defined to be acceptable.

○: SPF not less than 20
Δ: SPF not less than 10 and less than 20
X: SPF less than 10

In addition, the long-term stability was evaluated by leaving sunscreen cream at a constant temperature of 50° C. for one month and visually inspecting a change in the appearance. The long-term stability was evaluated according to the criteria shown below. Samples satisfying the criteria represented by ◎ or ○ were defined to be acceptable.

◎: No appearance change
○: Slight appearance change without a tendency of separation
Δ: A little of separation
X: Complete separation

TABLE 81

| Raw material | Example 40 | Example 41 | Example 42 | Comparative Example 41 |
|---|---|---|---|---|
| 1. Esterification reaction product (Production Example 1) | 5.0 | 5.0 | 5.0 | — |
| 2. Organic modified hectorite | 1.5 | 1.5 | 1.5 | 1.5 |
| 3. Liquid paraffin | 25.0 | — | — | 30.0 |
| 4. Squalane | — | 25.0 | 10.0 | — |
| 5. Dimethyl polysiloxane | — | — | 10.0 | — |
| 6. Trioctanoin | — | — | 5.0 | — |
| 7. Titanium dioxide | 5.0 | 5.0 | 5.0 | 5.0 |
| 8. 1,3-Butylene glycol | 15.0 | 15.0 | 15.0 | 15.0 |
| 9. Preservative | 0.5 | 0.5 | 0.5 | 0.5 |
| 10. Perfume | 0.1 | 0.1 | 0.1 | 0.1 |
| 11. Purified water | balance | balance | balance | balance |
| Total | 100.0 | 100.0 | 100.0 | 100.0 |

TABLE 82

| Sensory test | Example 40 | Example 41 | Example 42 | Comparative Example 41 |
|---|---|---|---|---|
| Effective length | ◎ | ◎ | ◎ | Δ |
| Adhesion | ◎ | ◎ | ◎ | Δ |
| Film-forming feeling | ◎ | ◎ | ◎ | ○ |
| SPF value | ○ | ○ | ○ | X |
| Long-term stability | ◎ | ◎ | ◎ | X |

The followings were confirmed by the results shown in Table 82.

It was recognized that the sunscreen cream (W/O type) of each of Examples 40 to 42 was excellent in effective length, adhesion to skin, and film-forming feeling (uniformity of cosmetic film), and the SPF values were high. These effects of the sunscreen cream (W/O type) of each of Examples 40 to 42 were higher than those of the sunscreen cream (W/O type) of Comparative Example 41.

Example 43 and Comparative Example 42

Production of Stick-Type Oil Concealer

Stick-type oil concealer having the formula shown in Table 83 was produced by the following process.

Raw materials 8 to 15 were heated to 70° C. and uniformly mixed to obtain mixture (A). Then, raw materials 1 to 7 and 16 were added to mixture (A), and the resulting mixture was uniformly mixed to obtain mixture (B). Mixture (B) was heated again for defoaming. The defoamed mixture was put into a stick-type container and then cooled to room temperature to obtain stick-type oil concealer. The results of sensory evaluation are shown in Table 84.

TABLE 83

| Raw material | Example 43 | Comparative Example 42 |
|---|---|---|
| 1. Esterification reaction product (Production Example 1) | 20.0 | — |
| 2. Esterification reaction product (Production Example 3) | — | 20.0 |
| 3. Bengara | 5.0 | 5.0 |
| 4. Yellow iron oxide | 3.0 | 3.0 |
| 5. Black iron oxide | 0.1 | 0.1 |
| 6. Stearic acid-treated titanium oxide | 10.0 | 10.0 |
| 7. Mica | 3.0 | 3.0 |
| 8. Candelilla wax | 2.0 | 2.0 |

TABLE 83-continued

| Raw material | Example 43 | Comparative Example 42 |
|---|---|---|
| 9. Microcrystalline wax | 2.0 | 2.0 |
| 10. Polyethylene wax | 4.0 | 4.0 |
| 11. Dipentaerythrite fatty acid ester | 5.0 | 5.0 |
| 12. Oxobenzone | 1.0 | 1.0 |
| 13. Dimethyl polysiloxane | 3.0 | 3.0 |
| 14. Cetyl 2-ethylhexanoate | 41.6 | 41.6 |
| 15. Preservative | 0.2 | 0.2 |
| 16. Perfume | 0.1 | 0.1 |
| Total | 100.0 | 100.0 |

TABLE 84

| Sensory test | Example 43 | Comparative Example 42 |
|---|---|---|
| Effective length | ◎ | Δ |
| Adhesion | ◎ | Δ |
| Color development | ◎ | ○ |
| Film-forming feeling | ◎ | Δ |

The followings were confirmed by the results shown in Table 84.

It was recognized that the stick-type oil concealer of Examples 43 was excellent in color development, adhesion to skin, and film-forming feeling (uniformity of cosmetic film), and the makeup was maintained for a long time. These effects of the stick-type oil concealer of Examples 43 were higher than those of the stick-type oil concealer of Comparative Example 42, and the makeup was maintained for a longer time.

Example 44 and Comparative Example 43

Production of Body Soap

Body soap having the formula shown in Table 85 was produced by the following process.

Raw materials 1 to 11 were uniformly mixed to obtain body soup. The results of sensory evaluation are shown in Table 86.

TABLE 85

| Raw material | Example 44 | Comparative Example 43 |
|---|---|---|
| 1. Esterification reaction product (Production Example 1) | 3.0 | — |
| 2. Cholesteryl hydroxystearate | — | 3.0 |
| 3. Lauric acid | 8.0 | 8.0 |
| 4. Myristic aid | 1.5 | 1.5 |
| 5. Palmitic acid | 1.5 | 1.5 |
| 6. Potassium hydroxide | 3.0 | 3.0 |
| 7. Coconut oil fatty acid diethanolamide | 1.0 | 1.0 |
| 8. Ethylene glycol distearate | 1.0 | 1.0 |
| 9. Preservative | 0.5 | 0.5 |
| 10. Perfume | 0.1 | 0.1 |
| 11. Purified water | balance | balance |
| Total | 100.0 | 100.0 |

TABLE 86

| Sensory test | Example 44 | Comparative Example 43 |
|---|---|---|
| Softness | ◎ | Δ |
| Moisturizing feeling | ◎ | ○ |
| Gloss | ○ | Δ |
| Cleansing properties | ○ | Δ |

The followings were confirmed by the results shown in Table 86.

It was recognized that the body soap of Example 44 was excellent in cleansing properties and imparted softness, moisturizing feeling, and gloss to skin by using it. These effects of the body soap of Example 44 were higher than those of the body soap of Comparative Example 43.

Example 45 and Comparative Example 44

Production of Body Powder

Body powder having the formula shown in Table 87 was produced by the following process.

Raw materials 3 to 6 were uniformly mixed and dispersed to obtain mixture (A). Raw material 1 or 2 was added to mixture (A), and the resulting mixture was pulverized to obtain body powder. The results of sensory evaluation are shown in Table 88.

TABLE 87

| Raw material | Example 45 | Comparative Example 44 |
|---|---|---|
| 1. Esterification reaction product (Production Example 1) | 5.0 | — |
| 2. Polyglyceryl-2 triisostearate | — | 5.0 |
| 3. Talc | 70.0 | 70.0 |
| 4. Mica | 19.9 | 19.9 |
| 5. Nylon powder | 5.0 | 5.0 |
| 6. Preservative | 0.1 | 0.1 |
| Total | 100.0 | 100.0 |

TABLE 88

| Sensory test | Example 45 | Comparative Example 44 |
|---|---|---|
| Effective length | ○ | Δ |
| Adhesion | ◎ | Δ |
| Spread | ◎ | ○ |

The followings were confirmed by the results shown in Table 88.

It was recognized that the body powder of Example 45 well adhered and spread on skin, and the makeup was maintained for a long time. These effects of the body powder of Example 45 were higher than those of the body powder of Comparative Example 44, and the makeup was maintained for a longer time.

Example 46 and Comparative Example 45

Production of Water-in-Oil Type Hand Cream

Water-in-oil-type hand cream having the formula shown in Table 89 was produced by the following process.

Raw material 1 or 2 and raw materials 3 to 7 were mixed. Then, raw material 8 was added thereto, and the resulting mixture was dispersed with a dispersion mixer to obtain mixture (A). The remaining raw materials were uniformly mixed and dispersed in mixture (A) to obtain water-in-oil-type hand cream. The results of sensory evaluation are shown in Table 90.

TABLE 89

| Raw material | Example 46 | Comparative Example 45 |
|---|---|---|
| 1. Esterification reaction product (Production Example 1) | 30.0 | — |
| 2. Esterification reaction product (Production Example 3) | — | 30.0 |
| 3. Squalane | 5.0 | 5.0 |
| 4. Vaseline | 1.0 | 1.0 |
| 5. Octamethylcyclopentasiloxane | 10.0 | 10.0 |
| 6. Cetyl isooctanoate | 10.0 | 10.0 |
| 7. Alkyl-containing polyoxyalkylene-modified organopolysiloxane | 3.0 | 3.0 |
| 8. Silica | 3.0 | 3.0 |
| 9. Ethyl alcohol | 5.0 | 5.0 |
| 10. 1,3-Butylene glycol | 5.0 | 5.0 |
| 11. Purified water | 27.9 | 27.9 |
| 12. Moisturizing ingredient (hyaluronic acid) | 0.1 | 0.1 |
| Total | 100.0 | 100.0 |

TABLE 90

| Sensory test | Example 46 | Comparative Example 45 |
|---|---|---|
| Moisturizing feeling | ◎ | ○ |
| Adhesion | ◎ | Δ |
| Softness | ○ | ○ |
| Film-forming feeling | ◎ | Δ |

The followings were confirmed by the results shown in Table 90.

It was recognized that the water-in-oil-type hand cream of Example 46 well adhered, moisturized, and softened skin, and film-forming feeling was maintained for a long time. These effects of the water-in-oil-type hand cream of Example were higher than those of the water-in-oil-type hand cream of Comparative Example 45.

The invention claimed is:

1. An esterification reaction product prepared by esterifying dipentaerythritol and a 12-hydroxystearic acid polymer and having a hydroxyl value of 20 to 70 mg KOH/g and an acid value of 3 mg KOH/g or less.

2. The esterification reaction product according to claim 1, wherein the hydroxyl value is 20 to 60 mg KOH/g.

3. The esterification reaction product according to claim 1, wherein the hydroxyl value is 25 to 50 mg KOH/g.

4. The esterification reaction product according to claim 1, wherein the hydroxyl value is 30 to 40 mg KOH/g.

5. The esterification reaction product according to claim 1, wherein the 12-hydroxystearic acid polymer has a polymerization degree of 2 to 12.

6. The esterification reaction product according to claim 1, wherein the 12-hydroxystearic acid polymer has a polymerization degree of 4 to 12.

7. The esterification reaction product according to claim 1, wherein the 12-hydroxystearic acid polymer has a polymerization degree of 6 to 12.

8. A cosmetic product containing an esterification reaction product according to claim 1.

9. The cosmetic product according to claim 8, wherein the content of the esterification reaction product is 0.1 to 80% by mass.

10. The cosmetic product according to claim 8, wherein the content of the esterification reaction product is 1 to 40% by mass.

11. The cosmetic product according to claim 8, wherein the cosmetic product is selected from the group consisting of lip cosmetics, foundation, emollient cream, milky lotion, makeup bases, hair cream, shampoo, hair rinse, hair conditioners, hand cream, serum, eyebrow and eye cosmetics, nail cosmetics, and sunscreen cosmetics.

* * * * *